(12) United States Patent
Marder Gilboa et al.

(10) Patent No.: US 11,954,926 B2
(45) Date of Patent: Apr. 9, 2024

(54) IMAGE FEATURE DETECTION

(71) Applicant: AIVF Ltd., Tel-Aviv (IL)

(72) Inventors: Daniella Marder Gilboa, RaAnana (IL); Ron Uriel Maor, London (GB); Ron Weiner, Tel Aviv (IL); Daniel S. Seidman, Tel Aviv (IL)

(73) Assignee: AIVF Ltd., Tel-Aviv (IL)

( * ) Notice: Subject to any disclaimer, the term of this patent is extended or adjusted under 35 U.S.C. 154(b) by 383 days.

(21) Appl. No.: 17/278,421

(22) PCT Filed: Sep. 20, 2019

(86) PCT No.: PCT/IB2019/057982
§ 371 (c)(1),
(2) Date: Mar. 22, 2021

(87) PCT Pub. No.: WO2020/058931
PCT Pub. Date: Mar. 26, 2020

(65) Prior Publication Data
US 2021/0390697 A1  Dec. 16, 2021

Related U.S. Application Data

(60) Provisional application No. 62/733,663, filed on Sep. 20, 2018.

(51) Int. Cl.
*G06V 20/69* (2022.01)
*G06T 5/50* (2006.01)
(Continued)

(52) U.S. Cl.
CPC .............. *G06V 20/695* (2022.01); *G06T 5/50* (2013.01); *G06T 7/0016* (2013.01); *G06T 7/248* (2017.01);
(Continued)

(58) Field of Classification Search
CPC ..... G06F 18/2413; G06T 7/0016; G06T 5/50; G06T 7/248; G06T 7/38;
(Continued)

(56) References Cited

U.S. PATENT DOCUMENTS 8,346,483 B2 * 1/2013 Kil .................. G01N 1/06
702/19
2011/0292047 A1 * 12/2011 Chang ................ G06V 30/268
345/424

(Continued)

FOREIGN PATENT DOCUMENTS

| JP | 2013/0502233 | 1/2013 |
| WO | WO 2017/132674 | 8/2017 |
| WO | WO 2020/058931 | 3/2020 |

OTHER PUBLICATIONS

Deep Learning Techniques for Automatic Classification and Analysis of Human in Vitro Fertilized (IVF) embryos. Prof. Sujata N Patil, Dr. Uday Wali, Dr. M K Swamy, Nagaraj S P& Dr. Nandeshwar Patil, Feb. 2018, vol. 5, Issue 2, JETIR (ISSN-2349-5162) (Year: 2018).*

(Continued)

*Primary Examiner* — Gandhi Thirugnanam
(74) *Attorney, Agent, or Firm* — PEARL COHEN ZEDEK LATZER BARATZ LLP

(57) ABSTRACT

A method, and corresponding apparatus, for identifying a feature in an image comprises determining a plurality of characteristic values for each pixel or group of pixels within the image, and determining a confidence value for a target area of the image on the basis of the plurality of characteristic values of the pixels within the target area. Each of the plurality of characteristic values relates to a different characteristic of the feature. The confidence value is indicative of whether the feature is represented by the target area of the image.

15 Claims, 9 Drawing Sheets

(51) Int. Cl.
  *G06T 7/00* (2017.01)
  *G06T 7/246* (2017.01)
  *G06T 7/38* (2017.01)
  *G06V 10/764* (2022.01)
  *G06V 10/82* (2022.01)

(52) U.S. Cl.
  CPC .............. *G06T 7/38* (2017.01); *G06V 10/764* (2022.01); *G06V 10/82* (2022.01); *G06T 2207/10016* (2013.01); *G06T 2207/20036* (2013.01); *G06T 2207/30024* (2013.01); *G06T 2207/30044* (2013.01)

(58) Field of Classification Search
  CPC . G06T 2207/10016; G06T 2207/20036; G06T 2207/30024; G06T 2207/30044; G06V 20/695; G06V 10/764; G06V 10/82
  See application file for complete search history.

(56) References Cited

U.S. PATENT DOCUMENTS

| | | | |
|---|---|---|---|
| 2014/0247972 A1 | 9/2014 | Wang et al. | |
| 2015/0175666 A1* | 6/2015 | Shai | C07K 14/005 514/20.7 |
| 2019/0244678 A1* | 8/2019 | Konvicka | G16B 30/00 |
| 2021/0390697 A1* | 12/2021 | Marder Gilboa | G06F 18/2413 |

OTHER PUBLICATIONS

Automated Monitoring of Early Stage Human Embryonic Cells in Time-lapse Microscopy Images, Aisha Sajjad Khan, A thesis submitted for the degree of Doctor of Philosophy at The Australian National University Sep. 2016 (Year: 2016).*

Retrospective analysis of outcomes after IVF using an aneuploidy risk model derived from time-lapse imaging without PGS, Alison Campbell a,*, Simon Fishel a, Natalie Bowman b, Samantha Duffy b, Mark Sedler b, Simon Thornton (Year: 2013).*

Blastocyst collapse is not an independent predictor of reduced live birth: a time-lapse study, Daniel Bodri, M.D., M.Sc., Ph.D., Takeshi Sugimoto, M.Sc., Jazmina Yao Serna, M.Sc., Satoshi Kawachiya, M.D., Ryutaro Kato, B.Sc., and Tsunekazu Matsumoto, M.D., Ph.D. (Year: 2016).*

International Preliminary Report on Patentability dated Apr. 1, 2021 From the International Bureau of WIPO Re. Application No. PCT/IB2019/057982. (10 Pages).

International Search Report and the Written Opinion dated Dec. 12, 2019 From the International Searching Authority Re. Application No. PCT/IB2019/057982. (13 Pages).

Khan et al. "Deep Convolutional Neural Networks for Human Embryonic Cell Counting", European Conference on Computer Vision, ECCV 2016, XP047354243, Part I, LNCS 9913: 339-348, Published Online Sep. 18, 2016.

Patil et al. "Deep Learning Techniques for Automatic Classification and Analysis of Human In Vitro Fertilized (IVF) Embryos", Journal of Emering Technologies and Innovative Research, JETIR, XP055639919, 5(2): 100-106, Feb. 2018.

Gardner et al. "Blastocyst culture and transfer: analysis of results and parameters affecting outcome in two in vitro fertilization programs"; published Oct. 1999; Fertility and Sterility vol. 72, Issue 4, pp. 604-609, USA.

Kirkegaard et al."Time-lapse parameters as predictors of blastocyst development and pregnancy outcome in embryos from good prognosis patients: a prospective cohort study"; published Jul. 30, 2013; Human Reproduction, vol. 28, Issue 10, pp. 2643-2651, USA.

Communication Pursuant to Article 94(3) EPC dated May 4, 2023 From the European Patent Office Re. Application No. 19779605.5 (4 Pages).

* cited by examiner

IMAGE FEATURE DETECTION

TECHNICAL FIELD

This invention relates to a method and system for detecting image features. In some examples, the system and method may be used to recognise morphological changes or morphokinetic parameters in an in-vitro embryo, However, aspects of the system and method may be broadly applicable.

BACKGROUND

The field of computer vision relates to the development of technologies and techniques that enable a computer to obtain detailed information from images or videos. One branch of this field relates to "feature detection" in which image processing is used to identify particular features or characteristics of an image or video. In recent years, many image processing techniques have been developed to identify the presence or characteristics of features in an image.

At present, existing image analysis methods often utilise machine learning algorithms and artificial neural networks. These approaches rely on "training" a system on a large sample of images, some of which contain the features in question. By providing the system with the knowledge of whether the image contains the feature, the system will "learn" how to identify the feature in future "unlearned" images. The more samples that are provided in the training phase, generally, the more reliable the system becomes at predicting the presence of the feature in subsequent images.

While these machine learning techniques are widely used, they suffer from several drawbacks. Firstly, the training process can be time-consuming and computationally intensive due to the large number of samples required to obtain reliable results. This also requires that many samples be available prior to the first use of the system. This is not necessarily the case in new fields of research or in areas where the samples are not easily accessible.

Secondly, these methods often struggle with processes such as edge detection in circumstances where a feature is subtle or not clearly defined. For example, while many current techniques may easily be able to identify and highlight the presence of a dog in an image, the same algorithm may struggle to pick out the presence or location of steam or smoke, because the feature boundary is not as clearly defined. A machine learning algorithm may be able to learn to do this, but it is likely to require an unrealistic number of sample images to train.

An example of an application in which these issues are prevalent is In-Vitro Fertilisation (IVF) Screening. In this procedure, an image of a fertilised embryo is analysed prior to implantation in order to determine the likelihood of success of the embryo during, and after, the implantation procedure. This is an area in which it is not always possible to obtain a large enough sample of successful and unsuccessful embryo images in order to train a machine learning algorithm. Furthermore, the features that need to be identified in the images (e.g. pronuclei) are often barely distinguishable, even to a skilled observer (i.e. an embryologist), and can be highly variable in their appearance. This means that even more samples would be required to train an algorithm to a reliable standard.

The present invention seeks to provide an improved system and method of feature detection in images.

SUMMARY

The present invention provides a method and system for identifying a feature in an image according to the appended claims.

According to one aspect of the present disclosure there is provided a method of identifying a feature in an image, comprising: determining a plurality of characteristic values for each pixel or group of pixels within the image, wherein each of the plurality of characteristic values relates to a different characteristic of the feature; and, determining a confidence value for a target area of the image on the basis of the plurality of characteristic values of the pixels within the target area, wherein the confidence value is indicative of whether the feature is represented by the target area of the image.

The characteristic value may relate to a probability of whether the pixel or group of pixels includes the respective characteristic.

Determining a plurality of characteristic values may comprise determining a log likelihood ratio for each characteristic for the pixel or group of pixels.

The log likelihood ratio may be determined on the basis of the pixel or group of pixels and a background area.

The one or more of the plurality of characteristic values may relate to a level of contrast between the pixel or group of pixels and the background area.

The different characteristics to which the characteristic values relate may correspond to one or more of: a border region of the feature; a high contrast portion of the feature; a roughness of the feature; and a smoothness of the feature.

The background area may be selected on the basis of the characteristic to which the characteristic value relates.

One or more of the plurality of characteristic values may relate to a lightness or darkness of the pixel or group of pixels relative to the background area.

The background area may be limited to neighbouring pixels of the pixel or group of pixels.

The neighbouring pixels may be located exclusively above or below the pixel or group of pixels.

Each of the plurality of characteristic values may be location specific with respect to the feature.

Determining the confidence value for the target area may comprise determining a location of each pixel or group of pixels relative to the target area; selecting the characteristic values which apply to each pixel or group of pixels on the basis of the location; using the selected characteristic values for the pixels or group of pixels to determine the confidence value.

Determining the confidence value may further comprise subtracting the characteristic values of the pixels outside of the target area.

The method may further comprise obtaining confidence values of a plurality of different target areas.

The different target areas may be differentiated by one or more of: position; size; and shape.

The target area may have a shape which corresponds to the feature.

The target area may be round.

The image may be an image of a sample. The method may further comprise: determining confidence values for corresponding target areas of different images of the sample.

The different images may be taken from different focal planes.

The different images may be temporally separated.

The image may be of a biological sample.

The biological sample may be an in-vitro embryo.

The one or more features may be pronuclei.

According to another aspect of the present disclosure there is provided an apparatus operable to perform a method in accordance with the present disclosure.

According to another aspect of the present disclosure there is provided a computer-readable medium comprising instructions which, when executed by a suitable computer, cause the computer to perform a method in accordance with the present disclosure.

According to one aspect of the present disclosure there is provided a system for identifying predictors of successful IVF implantation comprising obtaining a first sequence of time-stamped images tracking development of a pre-implantation embryo that has been qualified as being successfully implanted; obtaining a second sequence of time-stamped images tracking development of a pre-implantation embryo that has been qualified as being non-successfully implanted; computationally aligning the first sequence of time-stamped images with the second sequence of time stamped images such that the first sequence of time-stamped images and the second sequence of time-stamped images are development-time matched; and computationally processing each image of the first and the second sequences of time-stamped images in order to identify and track unique features of successfully implanted embryos thereby identifying predictors of successful IVF implantation.

Alignment may be effected by identifying a specific developmental feature in the first sequence of time-stamped images and the second sequence of time stamped images and setting a common development time based on the developmental feature.

The first sequence of time-stamped images and the second sequence of time-stamped images may be video sequences.

The first sequence of time-stamped images and the second sequence of time-stamped images may be time lapse sequences.

The unique features may be characterised by morphology, appearance time, disappearance time, magnitude of morphological change over time, time length of appearance, time length of morphological change and association with a genetic marker.

The image processing may be effected by a deep learning algorithm and/or by any of the methods of the present disclosure.

The system may further comprise modifying each image of the first and the second sequences of time-stamped images prior to processing. The modifying may be selected from the group consisting of colour shifting, colour filtering and embossing.

Another aspect of the present disclosure may provide a method of identifying predictors of successful IVF implantation comprising obtaining a first sequence of time-stamped images tracking development of a pre-implantation embryo that has been qualified as being successfully implanted; obtaining a second sequence of time-stamped images tracking development of a pre-implantation embryo that has been qualified as being non-successfully implanted; computationally aligning the first sequence of time-stamped images with the second sequence of time stamped images such that the first sequence of time-stamped images and the second sequence of time-stamped images are development-time matched; and computationally processing each image of the first and the second sequences of time-stamped images in order to identify and track unique features of successfully implanted embryos thereby identifying predictors of successful IVF implantation.

Aligning may be effected by identifying a specific developmental feature in the first sequence of time-stamped images and the second sequence of time stamped images and setting a common development time based on the developmental feature.

The first sequence of the time-stamped images and the second sequence of time-stamped images may be video sequences. The first sequence of time-stamped images and the second sequence of time-stamped images may be time lapse sequences.

The unique features may be characterised by morphology, appearance time, disappearance time, magnitude of morphological change over time, time length of appearance, time length of morphological change and association with a genetic marker.

It will be appreciated that except where mutually exclusive, a feature described in relation to any one of the aspects, examples or embodiments within the present disclosure may be applied to any other aspect, example, embodiment or feature. For example, the various aspects and features of the image analysis methods used to determine features of an image may be employed partially or in their entirety in the method and system for identifying predictors of successful IVF implantation, and vice versa.

Further, the description of any aspect, example or feature may form part of or the entirety of an embodiment of the invention as defined by the claims. Any of the examples described herein may be an example which embodies the invention defined by the claims and thus an embodiment of the invention.

BRIEF DESCRIPTION OF THE FIGURES

Exemplary embodiments of the invention are described herein with reference to the accompanying drawings in which:

FIGS. 5a'-5f' correspond to FIGS. 5a-5f and depict graphic representations of the images of a sample, wherein the pixels have various characteristic values;

FIG. 6' depicts a possible output from the methods described herein;

DETAILED DESCRIPTION

Figure 1:
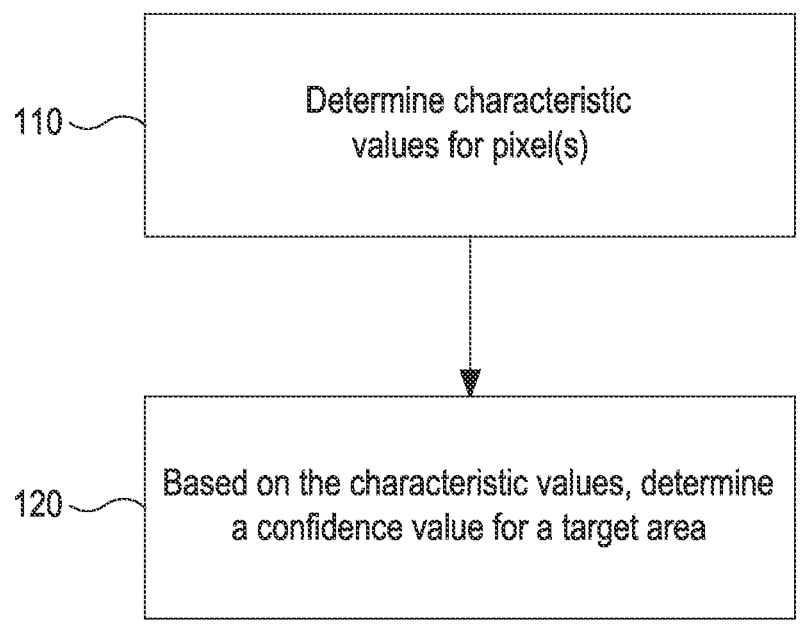
FIG. 1 depicts a method of identifying a feature in an image.

The present disclosure relates to an image analysis system or method which may be employed to determine a likelihood of whether a feature is present in an image. The system and method may be used to determine whether the feature has desirable or required characteristics, thereby allowing an assessment to be made as to whether the subject of the image is one of interest.

The system and method of the present disclosure are particularly suited to images which may have one or more features which are difficult to recognise visually by a human operator. The features may have a plurality of characteristics which are individually non-determinative of a subject but which may, when taken collectively with other characteristics, provide indication of the presence of the feature and or subject within an image. The indication of the presence of a feature may be provided by a likelihood or probability.

The system and method of the present disclosure may find use in identifying static or dynamic changes in an image. Thus, the method may be carried out on a single image or different images of a common subject. The different images may be taken from different aspects of the same subject (e.g. different focal planes, perspectives or magnifications) and/or be time separated images so that a dynamic aspect such as initiation, growth, degradation or motion may be observed. The time separated images may be time stamped images defined by predetermined stages of a process. The time separated images may be provided by a time lapse images or time lapsed video recording.

The subjects of interest may be biological in nature. Thus, the images may represent one or more biological structures, such as one or more cells, or a biological process such as in vitro fertilisation. Other applications are possible and some examples of such applications are contemplated herein.

Generally, within the context of the present disclosure, an image may be taken to be any visual representation of information relating to the form of an object. The image may be a photograph or other representation based on the capture of electromagnetic radiation such as an electronic image captured by a suitable camera or other device. The image may be obtained from a microscope such as an optical or electron microscope. The image may be obtained from a medical imaging system such as an ultrasonic, magnetic resonance or computer tomography. The image may be a drawing or other image obtained by means other than the direct capture of the form of a physical object. Furthermore, it is understood that "image" may refer to all or part of such a visual representation. That is to say, any method steps performed on an image may instead be performed on only part of an overall image. For example, a smaller portion of a photograph may be chosen as the subject of the method because it is a particular area of interest in the overall photograph. The image may be an image of a sample.

The image may be represented by image data in which the image is represented in some electronic form such as one or more of a matrix, vector or database which is storable within a computer memory and processed by one or more image processing techniques. The terms image and image data may be used interchangeably throughout the disclosure, where appropriate.

The image (or image data) may comprise a plurality of pixels or groups of pixels as is known in the art. A group of pixels may be a plurality of pixels that are directly adjacent to one another to define a single, continuous shape. The group of pixels may comprise two or more pixels. The two or more pixels may be chosen on the basis of an expected shape of a predetermined feature or parameter of the image. Unless stated otherwise, any reference to a pixel may also be construed as a reference to a group of pixels It is understood that a feature in an image may relate to any particular part or parts of the image which are of interest. For example, the feature may be an object, texture, colour, shape, or other thing depicted within the image. A feature in an image may be difficult to identify by human eye or by some computer vision techniques. This may be because the feature lacks clear boundaries or because the feature has similar properties to the remainder of the image which is not part of the feature. The feature may have a border region which defines the outermost boundaries of the feature.

Turning to FIG. 1, there is shown a method of identifying a feature in an image according to the present disclosure. The method may comprise: determining a plurality of characteristic values for each pixel or group of pixels within the image 110. Each of the plurality of characteristic values may relate to a different characteristic of the feature of interest in the image. The method may further comprise: determining a confidence value for a target area of the image on the basis of the plurality of characteristic values of the pixels within the target area 120. The confidence value may be indicative of whether the feature is represented by the target area of the image As noted, each of the plurality of characteristic values may relate to a different characteristic of the feature. The characteristics may be representative of various visible properties of the feature. The characteristics may relate to the colour, level of contrast, texture, roughness, smoothness, brightness, darkness or other visible properties of the feature. Additionally or alternatively, the characteristic may relate to one or more dimensions of the feature and/or properties which are location specific within the feature. For example, the characteristic may relate to a border region of the feature which may have attributes which are particular to a border region.

The characteristics may be represented by, or relate to, a characteristic value. The characteristic value may be a numerical value. For example, if a feature is identifiable by a characteristic black spot, the characteristic value may include a comparison of one or more pixels with surrounding pixels to determine a characteristic value in the form of a contrast between neighbouring pixels. Additionally or alternatively, the characteristic value may represent an extent of pixels which have a darkness within a predetermined range or some other parameter. A further characteristic value may be provided by the magnitude of darkness (or lightness) in the image or a relative darkness or lightness. Hence, the characteristic value may indicate to what extent a pixel or group of pixels includes a characteristic. The characteristic value may relate to a probability of whether the pixel or group of pixels includes the respective characteristic. The characteristic value may have a magnitude which correlates with how characteristic the pixel is of a pixel within the feature. The characteristic value may relate to a characteristic which is relative to a characteristic of a different pixel.

In some examples, higher characteristic values may be chosen to relate to a high likelihood that they are representative of the characteristic, and lower characteristic values may be chosen to relate to a low likelihood that they are not representative of the characteristic.

Once a characteristic value has been determined for the pixel, in step 120, a confidence value for a target area of the image may be determined on the basis of the plurality of characteristic values of the pixels within the target area.

The target area may represent a predetermined area in which a feature may be expected to be found. For example, where the feature of interest is known to have a particular shape, such as round or near round, the target area may be set as the shape and the shape investigated to determine which characteristics are present. The presence of the characteristics may be determined by looking at each of the pixels and/or groups of pixels and using the characteristic values of each to determine a confidence score for the target area.

The target area of the image may be a subset of the pixels in the image. The target area may be a subset of pixels which define a single, continuous shape. The target area may be a subset of pixels which define multiple discrete shapes. The target area may be an estimate for one or more of the position, size, thickness (e.g. of a wall or membrane), symmetry, shape, colour, texture, or orientation of the feature. Any number of target areas may be interrogated within the image.

The confidence value may be indicative of whether the feature is represented by the target area of the image. The confidence value may relate to, or be, the probability that the feature is represented by the target area of the image. The confidence value may have a magnitude which correlates with the likelihood that the feature is represented by the target area of the image.

Figure 2:
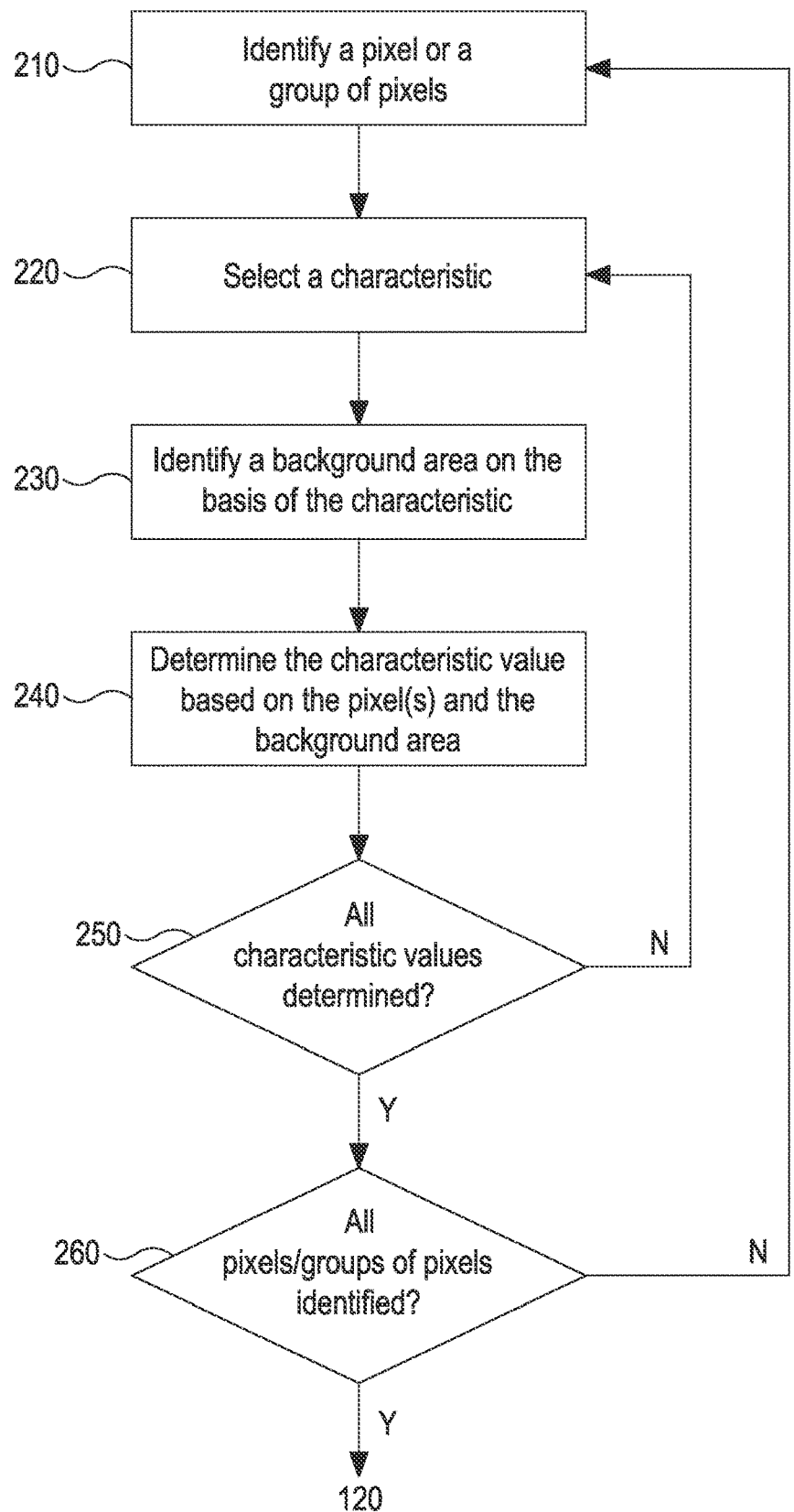
FIG. 2 depicts method steps for determining characteristic values for a pixel or group of pixels.

Turning now to FIG. 2, an example of a method for determining the characteristic values for a pixel or group of pixels will be described. In step 210, a pixel or group of pixels of the image is identified. The identification of the pixel or group of pixels may be done randomly or in predetermined pattern such as a raster scan in which each pixel or group of pixels is selected in turn line by line. Alternatively or additionally, the pixels can be selected by virtue of the position within the image or in relation to another feature within the image. For example, the image may include one or more markers which identify an area of likely interest within the image. The one or more markers may be naturally occurring within the subject of the image or may be introduced to highlight a particular area. The one or more markers may, for example, comprise a border feature which demarcates an area of interest. It will be appreciated that other scan patterns other than raster may be used. It will also be appreciated that the choice of whether to analyse a pixel or a group of pixels will be determined by feature of interest and characteristics of interest. For example, some characteristics may be detectable from a single pixel, others may be better detected as a group of pixels.

It will be appreciated from the above, that the selection of a characteristic as provided in step 220 of FIG. 2, may be carried out prior to the selection of the pixels. It will also be appreciated that the selection of the characteristic will be determined on the basis of the feature of interest, but for each feature there may be a pre-determined list of characteristics which may be selected in turn for each pixel or group of pixels.

In step 230, a background area may be selected. The background area may be selected on the basis of the characteristic which is of interest. Some characteristic values may be determined on the basis of pixels within a predetermined distance from the pixel or group of pixels. For example, to determine whether a black spot is present, it may be necessary to assess the darkness or contrast of the pixel in relation to other pixels within a predefined pixel radius. It is understood that predetermined distance or radius may be defined by, for example, distance measured across the image, or a particular number of pixels. For example, the predetermined distance may be determined by the size of the feature. The predetermined distance may be the radius or diameter of the feature. Alternatively, the predetermined distance may be 0.5×, 1.5×, 2× or another multiple of the radius or diameter of the feature.

In one example, when the feature to be located is 10 pixels across, the predetermined distance may be 10 pixels from the border of the feature. In other words, the background area may comprise all pixels within 10 pixels from the border of the feature. This provides a compromise between the need to stay proximate to the feature, in order to avoid irrelevant sections of the image, and the need to have a sufficient number of pixels within the background area to obtain a meaningful outcome.

In other examples, a characteristic may relate to the presence of the pixel in relation to a boundary or other element of the feature in which case the background may be selected with a predetermined geometrical relationship to the pixel, e.g. above, below, left or right.

For example, if the characteristic relates to a border region of the feature, then the background area may comprise only the pixels which are immediate neighbours of the pixel or group of pixels. In particular, the background area may be limited to neighbouring pixels which are located exclusively above or below the pixel or group of pixels. The background area may be limited in this way if the characteristic relates to whether the pixel is part of a top or bottom border region of the feature. It will be appreciated that the terms below, above, left and right may be used arbitrarily and in relation to the orientation of the image which is being analysed.

In another example, if the characteristic relates to a roughness or smoothness of the feature, then the background area may comprise all neighbouring pixels which directly neighbour the pixel or group of pixels (i.e. there are no intermediate pixels between the neighbouring pixels and the pixel or group of pixels). Alternatively, the background area may comprise all neighbouring pixels which directly or indirectly neighbour the pixel or group of pixels (i.e. there may be a predetermined range of pixels which are considered to be neighbouring).

In yet a further example, if the characteristic relates to a high contrast portion of the feature, then the background area may comprise the majority or all of the pixels within the image, besides the pixel or group of pixels in question.

In keeping with the above, the background area may be defined as part or all of the image remaining outside of the pixel(s) which have been selected for interrogation. The background area may comprise all of the pixels in the image which are not the pixel or group of pixels which have been selected. The background area may be limited to neighbouring pixels of the pixel or group of pixels. The background area may be selected on the basis of the selected characteristic (that is, the characteristic to which the characteristic value relates).

In step 240, once a background area has been selected, the characteristic value may be determined on the basis of the pixel or group of pixels and the background area. This determination may involve a comparison of the pixel or group of pixels with the background area. The characteristic value may relate to a level of contrast between the pixel and the background area. The characteristic value may relate to a brightness or darkness of the pixel relative to the background area.

Referring back to the above examples, in the case where the characteristic relates to a border region, in particular when the characteristic relates to whether the pixel is part of a top or bottom border, the pixel may be compared to the neighbouring pixels above and below the pixel. The pixel may then be assigned a characteristic value which indicates that the pixel is brighter or darker than the neighbouring pixels.

In the case where the characteristic relates to the roughness or smoothness, then the pixel may be compared to the neighbouring pixels to determine how similar the contrast of the pixel is to the contrast of the neighbouring pixels. A high characteristic value may be assigned if the pixel is similar in contrast to the neighbouring pixels. A low characteristic value may be assigned if the pixel is dissimilar in contrast to the neighbouring pixels. Alternatively, the high and low characteristic values may be assigned in reverse. In comparing the pixel to the neighbouring pixels, the average level of contrast of the neighbouring pixels may be taken.

In the case where the characteristic relates to a high contrast portion of the feature, the pixel may be compared to the average level of contrast of all of the pixels in the background area. This would indicate whether the pixel is a high contrast pixel in comparison to the rest of the image.

As noted previously, the characteristic values may be location specific with respect to the feature. The characteristics may be chosen such that the corresponding characteristic values are location specific with respect to the feature. In other words, a pixel may have a characteristic value which is indicative of where that pixel lies with respect to the feature. For example, a pixel which lies outside of the feature may be brighter or darker or rougher or smoother than a pixel which lies inside of the feature. A pixel which lies outside of the feature may have a level of contrast in relation to its neighbouring pixels which is greater or lesser than that of a pixel which lies inside the feature. Similarly, this example may apply to a pixel which lies inside the feature; on the border of the feature; inside or outside of a certain distance from the feature; at the centre of the feature; or elsewhere with respect to the feature. In this way, the characteristic values may individually, or collectively, serve as an indicator of approximately where a pixel may lie with respect to the feature.

Once a characteristic value has been determined of a pixel or group of pixels, it may be queried, at step 250, as to whether all characteristic values of interest for that pixel or group of pixels have been determined. If not all of the characteristic values have been determined then the process may return to step 220 to select a further characteristic and repeat the process as above.

If all of the characteristic values have been determined, it may be queried, at step 260, as to whether all pixels or groups of pixels have been identified. That is to say, whether characteristic values have been assigned to all of the pixels within the image or within the area of interest in the image. If there are more pixel(s) remaining in the image which have not yet had characteristic values assigned, the process may repeat from step 210 until all pixels are considered. If all of the pixels have had characteristic values assigned, the process may move onto step 120.

Figure 3:
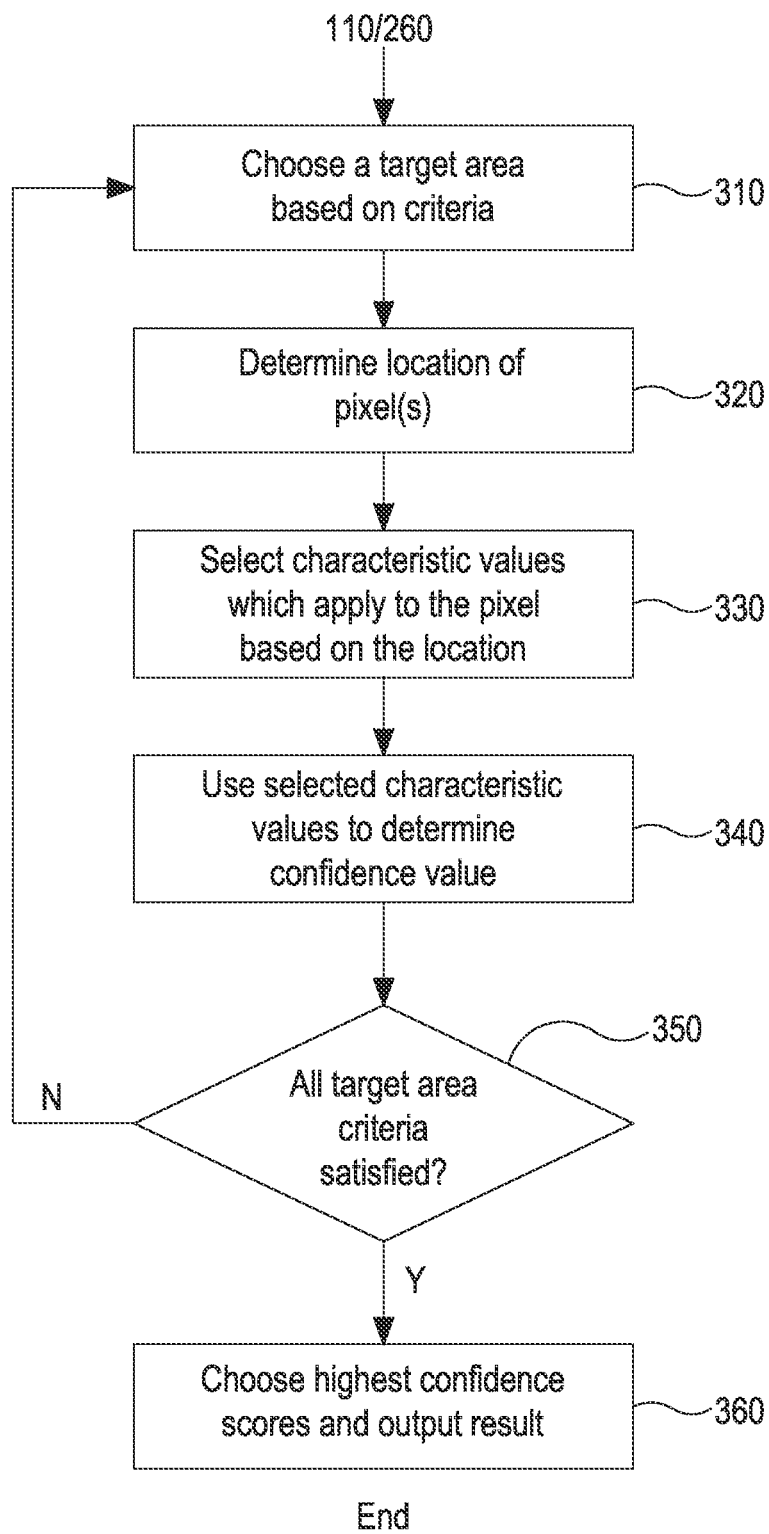
FIG. 3 depicts method steps for determining a confidence value for a target area of an image.

Turning now to FIG. 3, an exemplary method for determining a confidence value for a target area will be described. Once characteristic values have been determined for all of the required pixels, these characteristic values may be used to determine a confidence value for one or more target areas. In step 310 of this process, a target area is chosen. As described above, the target area may define a subset of pixels within the image. The target area may comprise a border which encloses the subset of pixels.

The target area may be chosen on the basis of one or more criteria for setting the target area. The one or more criteria may be dependent on known criteria satisfied by the feature. In other words, the target area may be chosen to be representative of a possible configuration of the feature. The criteria, for example, may define the geometric shape of the target area. Such a shape criteria may dictate that all target areas share the same shape. The shape criteria may dictate which shape this is. The target area may, for example, be round. For example, the target shape may be circular or oval or race-track shaped. Alternatively, the target area may be other shapes. This shape may be chosen on the basis of the known shape of the feature. In other words, the target area may have a shape which corresponds to the feature. Furthermore, the shape criteria may instead dictate that the target area could be any one of a plurality of shapes. In such an instance, the target areas which are identified may all have different shapes. For example, if it is known that the feature could be circular, square or triangular, then one or more target areas of each of those shapes may be chosen.

As well as, or instead of, shape, the criteria may be based on other properties. For example, the criteria may relate to the location of the target area with respect to the image. The criteria may be dependent on the number of target areas which would fit into the image. This may or may not allow the target areas to overlap. The criteria may relate to one or more of the position, size, shape, colour, texture, or orientation of the target area.

Once a target area has been selected, the location of the pixels relative to the target area may be determined in step 320. This determination may be performed for all pixels within the image. Alternatively, this determination may only be performed for some of the pixels in the image, which may be in an area of interest of the image. Possible locations of the pixels may include: within the target area; outside of the target area; on the border of the target area; inside or outside of a predetermined distance from the target area; and/or at the centre of the target area. Such locations may be further specified with more granularity. For example, a pixel "within the target area" may be determined to be within a predetermined region within the target area. This region may be upper or lower halves, a predetermined quadrant, a predetermined radial range from the centre of the target area, or another region within the target area.

When considering whether a particular pixel is part of the feature, it is possible that only some of the characteristic values will be relevant. Therefore, after the location of the pixels has been determined, characteristic values may be selected which apply to each pixel on the basis of the location 330. That is, characteristic values may be selected if they are relevant based on the location of the particular pixel in question, in relation to the target area. For example, the characteristic values may be chosen based on whether the pixel is in the target area or outside the target area. The characteristic values may be chosen based on the particular location within the target area, or the particular location outside the target area. In one example, as noted above, if the feature includes a boundary having particular characteristics, the pixels in the boundary region of the target area may have characteristic values representative of a boundary condition selected for determining the confidence score. Other characteristic values which have been determined for the pixel but which are not relevant to a boundary region may be disregarded. Alternatively such characteristic values may be used to provide or reinforce a determination that the pixel is not a boundary pixel. Hence, if there is a high confidence value that a particular pixel forms a dark spot, this may be used to show that the pixel is not a boundary pixel.

Proceeding to step 340, the selected characteristic values for the pixels may be used to determine a confidence value. As described above, the confidence value may be indicative of the likelihood, or probability, that the chosen target area is representative of the feature. The process of using the characteristic values to determine a confidence value is described in more detail below, with reference to FIG. 4.

Having determined a confidence value, it may be queried, in step 350, whether all the target areas of interest, e.g. all the criteria for choosing a target area, have been investigated. In other words, it is determined whether the target area(s) that have been chosen so far cover all permutations of the criteria. If they have not all been investigated, the method returns to step 310, a different target area is chosen and the process repeats. Thereby, the method may comprise obtaining confidence values of a plurality of different target areas.

The different target areas and selection thereof may be carried for all permutations but in practice the target areas will be investigated within ranges of criteria. For example, in an investigation of whether an in-vitro embryo is viable, it may be that a pronucleus must be circular and have given size. Hence, the criteria may comprise a permissible range of sizes and permissible shapes as defined by an already known range. Additionally or alternatively, the presence of a pronucleus in a viable embryo may be known to exist only in a particular area or areas of the image either generally or in relation to one or more other elements or features of the image. Thus, the portions of the image through which the target area is swept may be limited to a predetermined range.

In keeping with the above, the different target areas may be differentiated by one or more of the criteria. The different target areas may, in particular, be differentiated by one or more of: position; size; and shape. For example, the target area criteria may specify that the target areas must be: a circle, within a radius in a certain range, and be located in one of several different locations within the image. In step 310, a first target area will have been chosen which satisfies these criteria. In step 350, it will be determined that only one target area has so far been chosen to match these criteria, and therefore they have not all been satisfied (i.e. not all permutations have been covered). The process will return to step 310, in which another target area will be chosen. This next target area may be a circle with a different radius and/or it may be a circle in a different location. Step 350 may only return "yes" as its outcome once all permutations of the criteria have been satisfied (i.e. in this instance, there is a target area for all radii within the range, at each and every location specified). Alternatively, step 350 may only return "yes" as its outcome once a predefined number of permutations has been satisfied.

If all of the target areas have all been investigated, the relevant outputs may be selected from the data which has been gathered and outputs returned. The relevant outputs may be returned to a user, possibly by means of a graphical user interface, or to a computer or other data processing unit. It is understood that by "all criteria" being satisfied, this may instead be a predetermined number of the criteria, or only certain permutations of each of the criteria.

In some examples, prior to outputting the results, the method may be repeated on the same image. The method may be repeated to, for example, test the reliability of the results, or to improve the accuracy or confidence of the result. The method may be repeated to allow a user to change, expand, or narrow the target area criteria based on the results of the first run.

In some examples, the method may be repeated on one or more different images. The first image may be an image of a sample. The one or more different images may be images of the same sample. The different images may be taken from different focal planes and/or different perspectives or viewpoints. The feature may be visible in varying degrees in each of the different focal planes and/or different perspectives or viewpoints. By using different focal planes, this increases the number of images that the method may be applied to, potentially improving the resultant confidence values. Furthermore, this may allow a high confidence value to be achieved even though the feature is not perceivable in any one image. Similar benefits may be made for images taken at different magnifications.

The different images may be temporally separated. The images may capture any temporal development or changes of the feature. Parameters of the method (e.g. characteristic selected, characteristic values determined, target area criteria, target areas chosen) may be altered, removed or added for each different image according to the temporal separation. In other words, parameters of the method may be time dependent. For example, the shape of the target areas chosen may be changed for each temporally separated image if it is known that the shape of the feature may change with time. For example, it may be known that the feature is a circle for a first time-period and then changes to be an oval after this time-period. The target area may then be chosen to satisfy being a circle in the first time period, and being an oval afterwards. Further parameters of interest and the use of time lapsed images are provided below.

In examples where the conclusion results in the return of relevant outputs, these outputs may be data. For example, the method may return data representative of the location of each target area, along with data which indicates a confidence value for each target area. The method may return data representative of the characteristics and/or characteristic values of each pixel. The outputs may be processed to provide a graphical representation of the result. The method may return a graphical representation indicating the location of the target area relative to the feature and/or the image. The graphical representation may contain a graphical indication of the confidence value associated with that target area. For example, the graphical indication may be the colour or brightness of graphical representation of the target area. The graphical representation may be a so-called 'heatmap' which provides a visual indication of the relevant characteristic values and/or confidence values within a target area.

At step 360, an additional method step of selecting a target area which has the highest confidence value is provided. By highest, it is meant that the confidence value indicates that this target area is most likely to be representative of the feature of interest. The method may then only return the target area and/or confidence value which is most likely to be representative of the feature. Alternatively, the additional method step may select one or more target areas which have a confidence value above a predetermined threshold. The method may then return the target areas and/or confidence values which are above this predetermined threshold.

Figure 4:
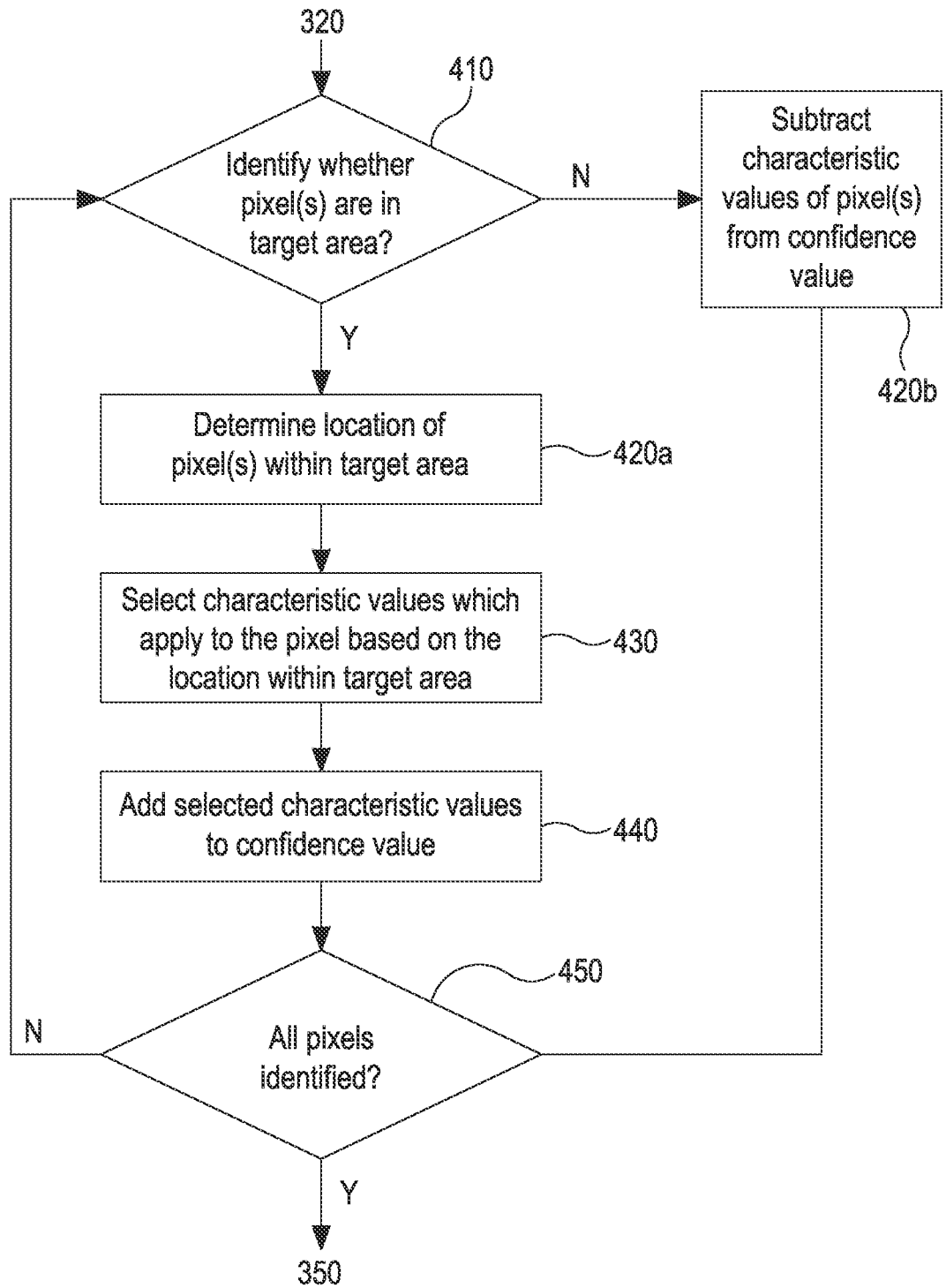
FIG. 4 depicts method steps for using characteristic values to determine a confidence value of an image.

Turning now to FIG. 4, exemplary method steps are depicted which may replace steps 330 and 340 as shown in FIG. 3. The exemplary steps in FIG. 4 show in more detail the steps which may be taken to select characteristic values and use them to determine a confidence value. FIG. 4 may carry on from step 320 in which the location of the pixels is determined.

Determining the confidence value may thereby further comprise subtracting the characteristic values of the pixels outside of the target area. Hence, in step 410, it may be queried as to whether the pixels are located within the target area or not. If it is identified that the pixels are not located in the target area, the process may proceed to step 420*b*. In this step, the characteristic values of the pixels may be subtracted from the confidence value.

The characteristic values of the pixels may be subtracted from the confidence value for all of the pixels that are located anywhere outside of the target area. Alternatively, the characteristic values may be subtracted from the confidence value for only a selection of the pixels that are located outside of the target area. This may, for example, involve only subtracting the characteristic values associated with pixels which neighbour the target area. It is understood that "neighbour" may mean that the pixels are immediately adjacent to the target area, or it may mean that the pixels are within a predetermined distance from the target area.

In cases where a pixel has been assigned a characteristic value which is negative, it will be understood that subtracting this characteristic value from the confidence value is effective to adding the absolute magnitude of that characteristic value.

If, instead, it is identified that the pixels are located within the target area, the method proceeds to step 420a. In this step, the location of the pixels within the target area may be determined. The location may identify the approximate location of the pixel relative to features of the target area. For example, the pixel may be determined as being located: within the target area; on the border of the target area; at a particular location on the border of the target area (e.g. upper border, lower border, left border, right border); in a particular half or quadrant or other fraction of the target area; at the centre of the target area; and/or within a particular distance from the centre of the target area.

Once the location of the pixel within the target area has been determined, the method proceeds to step 430, in which characteristic values are selected based on the location within the target area. As mentioned above, it may be the case that only one or some of the characteristic values are relevant based on the location of the pixel within the target area.

For example, if the pixel is on an upper border of the target area, it may be relevant to consider the pixels contrast relative to the neighbouring pixels directly above and below this border pixel (i.e. to see whether there is a significant change in contrast, which may indicate the presence of a border). In this example, a characteristic value may be selected which is representative of this property. It may also be of interest to consider the contrast relative to the neighbouring pixels directly either side of the border pixel (i.e. to see whether the contrast is largely the same, which may indicate the border continues along this direction). On the other hand, a characteristic value which, for example, is indicative of a contrast compared to the average contrast in that region may not be of interest for a border pixel as it might not give an indication of whether the pixel represents a border or not. Therefore, in this example, this characteristic value may not be selected for this pixel. A similar process of selecting characteristic values would be applied if the pixel was instead located elsewhere other than the border, but different values may have been selected. Proceeding to step 440, the selected characteristic values for this pixel are added to the confidence value. Once this is completed, it may be queried in step 450 as to whether all pixels have been identified.

If they have not, the process may repeat to continue to add/subtract the characteristic values of the pixels from the confidence value. Once all of the pixels have been identified, the process moves on to step 350, as depicted and described with respect to FIG. 3.

This process of adding or subtracting selected characteristic values to or from the confidence value results in the calculation of a confidence value which may be indicative of whether the target area represents the feature. In particular, the characteristic values may have a magnitude which correlates with how likely the pixel is to represent a pixel in the feature and so, when these characteristic values are combined in this way, the resultant confidence value may have a magnitude which correlates with how likely the target is to represent the feature as a whole.

An example of a type of value which would satisfy the above, is a log likelihood ratio. One or more of the characteristic values, and/or the confidence values, may be a log likelihood ratio. Determining the characteristic values may comprise determining a log likelihood ratio of the characteristic for the pixel for features in which the probability of the pixel or group of pixels being representative of a characteristic vs the background area is provided.

A log likelihood ratio is a test statistic calculated from the likelihood of a first hypothesis, $H_0$, and the likelihood of a second hypothesis, $H_1$. The log likelihood ratio, LLR, is then given by:

$$LLR = \ln\left(\frac{H_0}{H_1}\right)$$

The log likelihood ratio is defined only up to a factor of a constant. That is to say, in some versions of the above calculation, the natural logarithm may be multiplied by a constant. For example, the natural logarithm may be multiplied by −2. Taken in its current form, it is apparent from the equation that the log likelihood ratio will be: large in magnitude and positive when the first hypothesis is most likely; small in magnitude when the first and second hypotheses are similarly likely; and large in magnitude and negative when the second hypothesis is most likely. In this way, the log likelihood ratio can be seen as representative of the likelihood, or probability, that the first hypothesis is satisfied.

When considering characteristic values, the first hypothesis may be that the pixel in question belongs to the feature, and the second hypothesis may be that the pixel in question does not belong to the feature. The likelihoods $H_0$ and $H_1$ are therefore the likelihoods that the pixel belongs or does not belong to feature, respectively, based on the characteristic being considered. In practice, these likelihoods may be determined in advance based on known characteristics of a feature. That is to say, it may be known that certain characteristics are typical of the feature. It would therefore be possible to assign the likelihoods to the pixel based on whether the pixel similarly shares these certain characteristics.

In another example, consider the characteristic of the smoothness of the pixel, when it is known, say, that the feature is smooth. By "smoothness" it is meant how similar the pixel is to its neighbouring pixels. If a pixel is similar in, for example, contrast, colour, and/or brightness to its neighbouring pixels provided in the selected background area, then the pixel may be considered smooth. If the pixel is not similar in these regards then the pixel may be considered rough. If the pixel in question is smooth, the pixel will be assigned a high value for $H_0$ and a low value for $H_1$ (since it is more likely, based on smoothness alone, that the pixel belongs to the feature than not). The log likelihood ratio will therefore be large and positive, indicating that the pixel is likely to belong to the feature based on this characteristic alone.

In the same example, if the pixel in question is rough, the pixel will be assigned a low value for $H_0$ and a high value for $H_1$ (since, in this case, it is more likely, based on smoothness alone, that the pixel does not belong to the feature). The log likelihood ratio will therefore be large and negative, indicating that the pixel is unlikely to belong to the feature based on this characteristic alone.

Again, in the same example, if the pixel in question is neither particularly rough, nor particularly smooth, the pixel will be assigned values of similar magnitude for both $H_0$ and $H_1$ (since it is similarly likely, based on smoothness alone, that the pixel does or does not belong to the feature). The log likelihood ratio will therefore be of low magnitude, and potentially negative or positive, indicating that the pixel is neither particularly likely, nor particularly unlikely, to belong to the feature based on this characteristic alone.

In some examples, the likelihoods may be based on the frequency or prevalence of a particular pixel inside or outside of the target area. For example, if the pixel has an associated characteristic which is common inside the target area and is uncommon outside of the target area then the ratio of $H_0:H_1$ will be high for that pixel. In another example, if the characteristic is say 1000 times more common inside than outside then LLR=ln 1000. If the characteristic is 1000 times more common outside than inside then LLR=ln 1/100=−ln 1000. This frequency or prevalence may be calculated by counting pixels of different values across sample images.

When the log likelihood ratios that make up the characteristic values are added and subtracted from one another as described above, they result in a log likelihood ratio which forms the confidence value. Based on the example calculation above, this means that the confidence value will be large and positive if the target area is very representative of the feature, small if the target area is weakly representative of the feature, and large and negative if the target area is very unrepresentative of the feature.

In the first case considered above (where the pixel is smooth, characteristic of the feature, and thus assigned a large, positive log likelihood ratio), if the characteristic value is added to the confidence value (because the pixel is within the target area) then the confidence value will increase. This indicates that, based on the contribution of this pixel and characteristic value, the target area is more likely to be representative of the feature. Alternatively, if the characteristic value is subtracted from the confidence value (because the pixel is not within the target area) then the confidence value will decrease. This indicates that, based on the contribution of this pixel and characteristic value, the target area is less likely to be representative of the feature. In this way, a pixel which is characteristic of the feature increases the confidence if it is predicted to be in the feature, and decreases the confidence if it is predicted to be outside of the feature.

In the second case considered above (where the pixel is rough, not characteristic of the feature, and thus assigned a large, negative log likelihood ratio), if the characteristic value is added to the confidence value (because the pixel is within the target area) then the confidence value will decrease. This indicates that, based on the contribution of this pixel and characteristic value, the target area is less likely to be representative of the feature. Alternatively, if the characteristic value is subtracted from the confidence value (because the pixel is not within the target area) then the confidence value will increase. This indicates that, based on the contribution of this pixel and characteristic value, the target area is more likely to be representative of the feature. In this way, a pixel which is not characteristic of the feature decreases the confidence if it is predicted to be in the feature, and increases the confidence if it is predicted to be outside of the feature.

In the third case considered above (where the pixel is neither particularly rough nor smooth, is not particularly characteristic or uncharacteristic of the feature, and thus assigned a log likelihood ratio low in magnitude), the confidence value changes little regardless of whether the characteristic value is added or subtracted. In this way, a pixel which may or may not be characteristic of the feature does not substantially impact the confidence value.

An exemplary graphic depiction of the method is shown in FIGS. 5, 5', 6 and 6'. FIGS. 5a-5f and 6 represent simplified schematics of the graphic depiction that is shown in FIGS. 5a'-5f' and 6'. It is understood that any reference to features in FIGS. 5a-5f apply to the features of the primed figures, and vice versa. For brevity, the corresponding description is not repeated for each set. Starting with FIGS. 5a-5f, these figures depict examples of method step 110 (and its corresponding detailed counterpart steps in FIGS. 2-4). In each FIG. 5a-5f, an image has been divided up into a plurality of pixels or groups of pixels and each pixel (or group thereof) has been assigned a characteristic value based on the corresponding characteristic. The different characteristics to which the characteristic values relate may correspond to one or more of: a border region of the feature; a lightness of the feature; a darkness of the feature; a high contrast portion of the feature; a roughness of the feature and a smoothness of the feature. Examples of characteristic values which may relate to such characteristics are described below with reference to FIGS. 5a-5f.

Figure 5A:
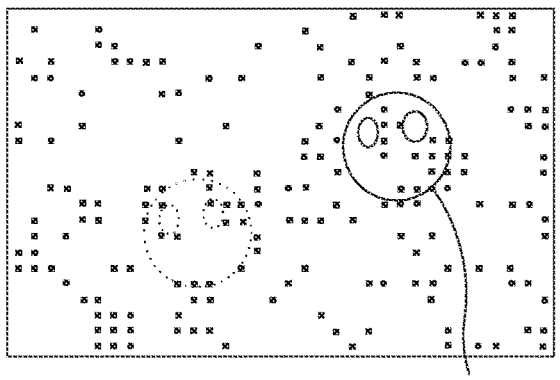
FIGS. 5a-5f depict simplified schematics of graphic representations of the images of a sample, wherein the pixels have various characteristic values.
Figure 5B:
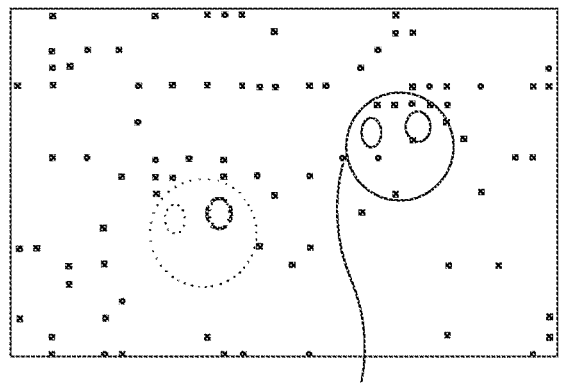
Figure 5C:
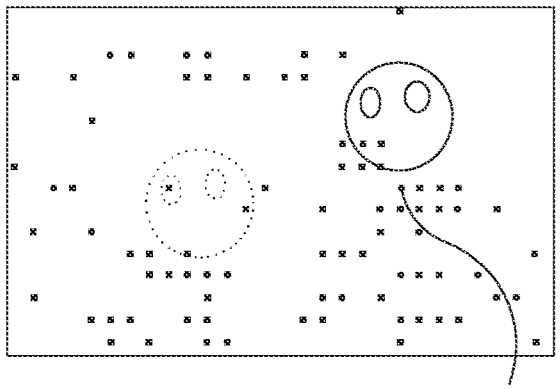
Figure 5D:
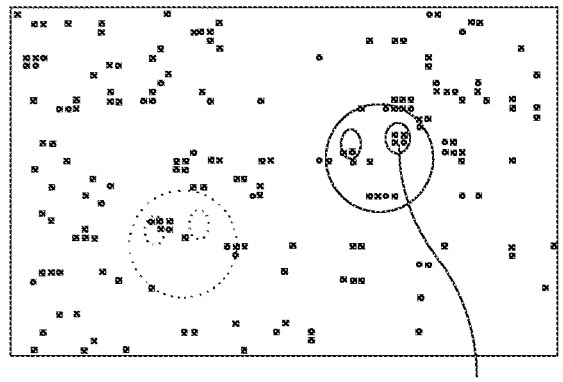
Figure 5E:
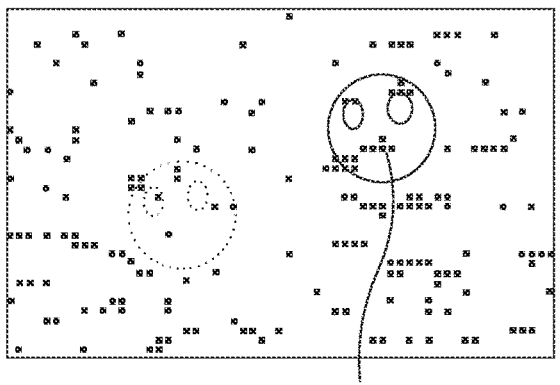
Figure 5F:
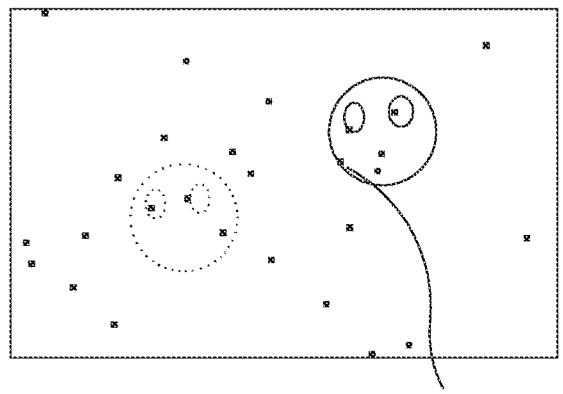
Figure 5A:
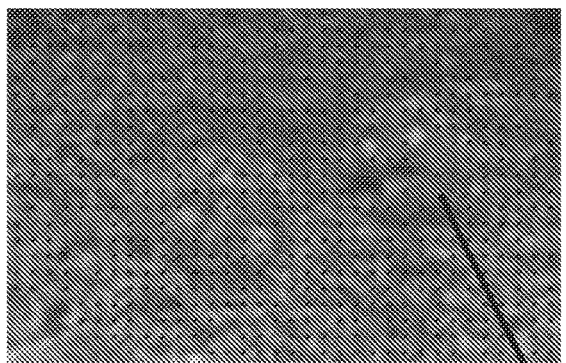
Figure 5B:
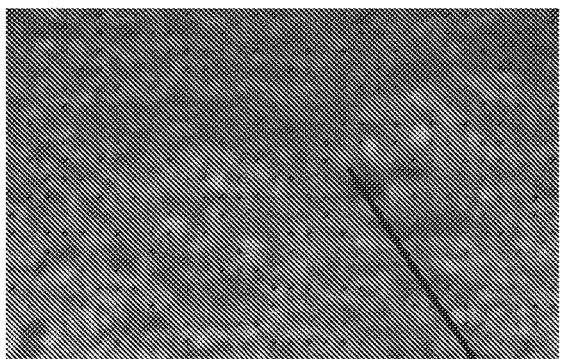
Figure 5C:
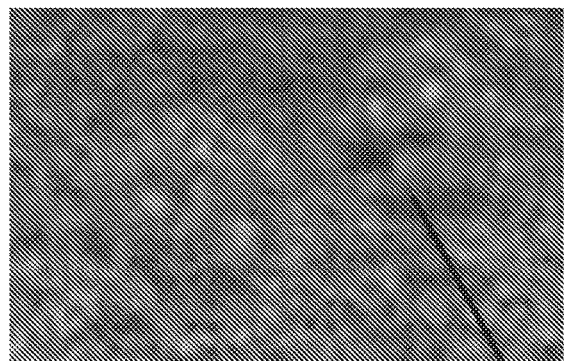
Figure 5D:
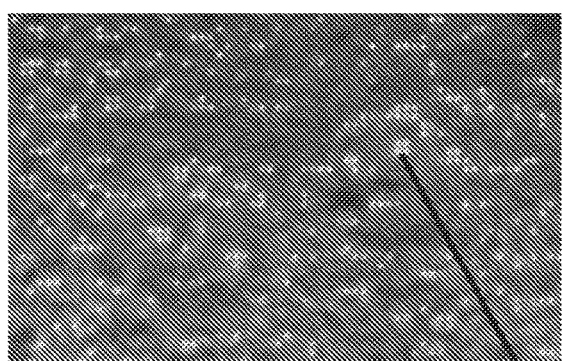
Figure 5E:
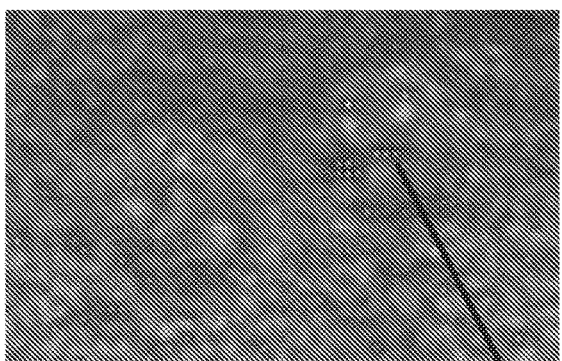
Figure 5F:
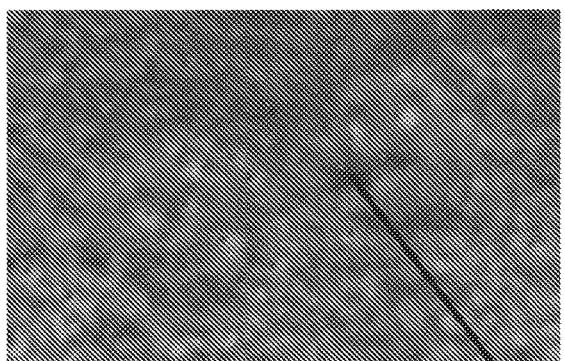

Some of the pixels have been overlaid with a visual indicator 510-560. In the example shown, the magnitude of this characteristic value corresponds to the brightness of the visual indicator 510-560 of these pixels. The characteristic values being considered in each Figure are as follows:

FIG. 5a—smoothness (i.e. similarity to neighbouring pixels)—brighter visual indicator 510=smoother pixel FIG. 5b—lightness compared to regional average—brighter visual indicator 520=lighter pixel FIG. 5c—darkness compared to regional average—brighter visual indicator 530=darker pixel FIG. 5d—lightness compared to pixels above and below—brighter visual indicator 540=lighter pixel FIG. 5e—darkness compared to pixels above and below—brighter visual indicator 550=darker pixel FIG. 5f—particularly dark or light spots compared to regional average—brighter visual indicator 560=significantly lighter/darker pixel than regional average FIGS. 5a-5f provide an example of how these values may be represented in a graphical form, in this case, as a heatmap. By combining these characteristic values (thereby combining the heatmaps) as described herein, a further heatmap of confidence values may be obtained. If, as described in detail above, these confidence values are used to select one or more target areas which are representative of the feature then it is possible to obtain a representation as shown in FIG. 6.

In some examples of the present disclosure, the image is of a biological sample. For example, the biological sample may be an embryo. The biological sample may be an embryo when the method is being used prior to IVF screening, for example. The embryo may be an in-vitro embryo. Alternatively, the biological sample may be a single cell. For example, the biological sample may be an unfertilised ovum or a sperm cell. The biological sample may be one or more of any of the above. The one or more features as described in the method above may be pronuclei.

Figure 6:
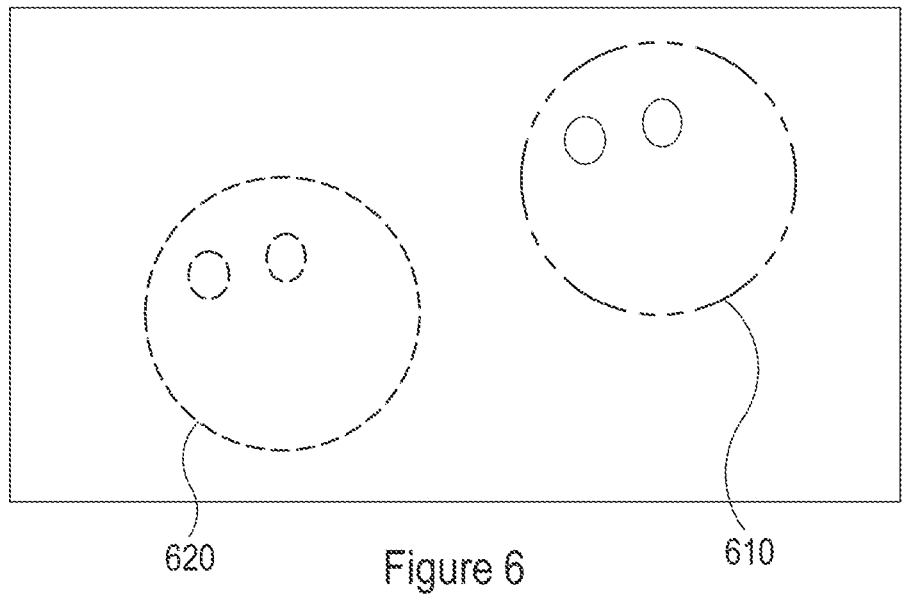
FIG. 6 depicts a simplified schematic of a possible output from the methods described herein.
Figure 6:
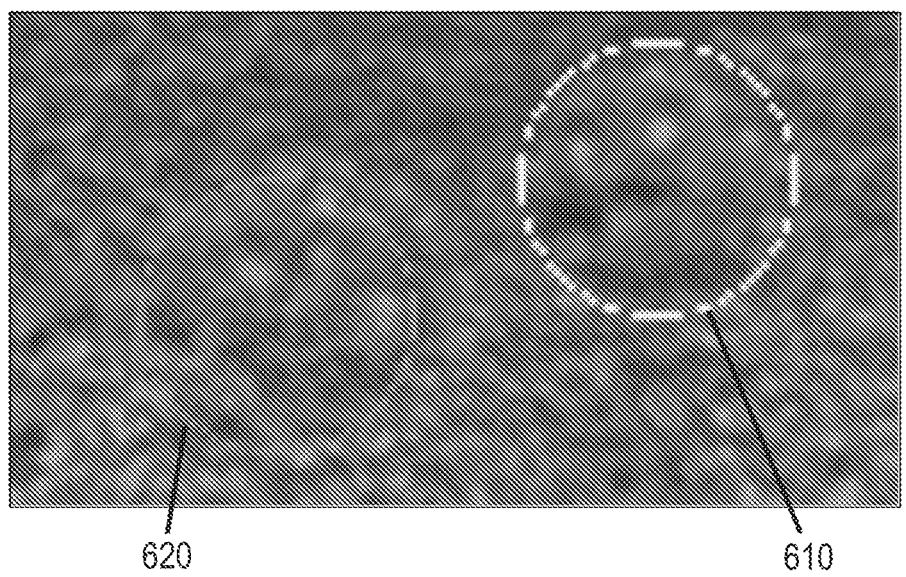

FIG. 6 depicts a possible output of the methods as described herein. By applying the above methods, it is possible to obtain one or more predictions for the location of the feature, based on the one or more target areas that may be selected for having the highest confidence values, or for having confidence values above a predetermined threshold. In this example, two target areas 610 and 620 have been identified. The target areas 610 and 620 have been highlighted to visually depict the location, size and shape of the feature within the image. Target area 610 has a higher confidence value than target area 620, and is therefore brighter than target area 620. In this way, it is possible to depict to the end user possible locations of the features and provide a visual representation of how likely it is that the predictions match the actual feature.

It will be readily apparent to the skilled person that the above method may be used in many different applications. Examples of such applications include: in manufacturing, for finding imperfections in industrial materials; in automated vehicles, for tracking the location and movement of objects for collision avoidance, in security and surveillance, for detecting unwanted intruders; in weather monitoring, for detecting particular weather patterns; in recreational photography, for identifying items of interest in a photograph; in nature observation, for identifying animal or plant types; and in any other application where the features of interest are of a variable and indistinct nature.

As mentioned previously, one example of an application of this methodology is in the field of IVF screening. The procedure of IVF involves fertilising an ovum with sperm outside of the human or animal body, to form a pre-implantation embryo. This embryo is then implanted into a host surrogate to allow gestation of the embryo. However, the IVF process has a poor success rate and many implantations do not result in full gestation up to live birth. An IVF embryo which results in a clinical pregnancy as defined by ultrasound at 6 weeks and/or live birth is often considered to be a successful embryo. An embryo which does not result in these outcomes is accordingly considered unsuccessful.

Due to the expensive, and often traumatising, impacts of IVF treatment, IVF screening techniques have been developed in order to predict, before implantation, whether an embryo is likely to be successful or unsuccessful. Such techniques usually require a highly qualified and experience embryologist to examine images of the embryo and identify features which are predictors of the likelihood of success of the embryo.

One of the major difficulties suffered by these techniques is that the identification of these features can be very challenging. The features present in the images are often very subtle and variable in appearance, and are often barely perceptible even to a skilled embryologist. Therefore, a difficulty which is often faced before the embryologist can begin to assess the viability of the embryo, is identifying the features in the images.

Figure 7:
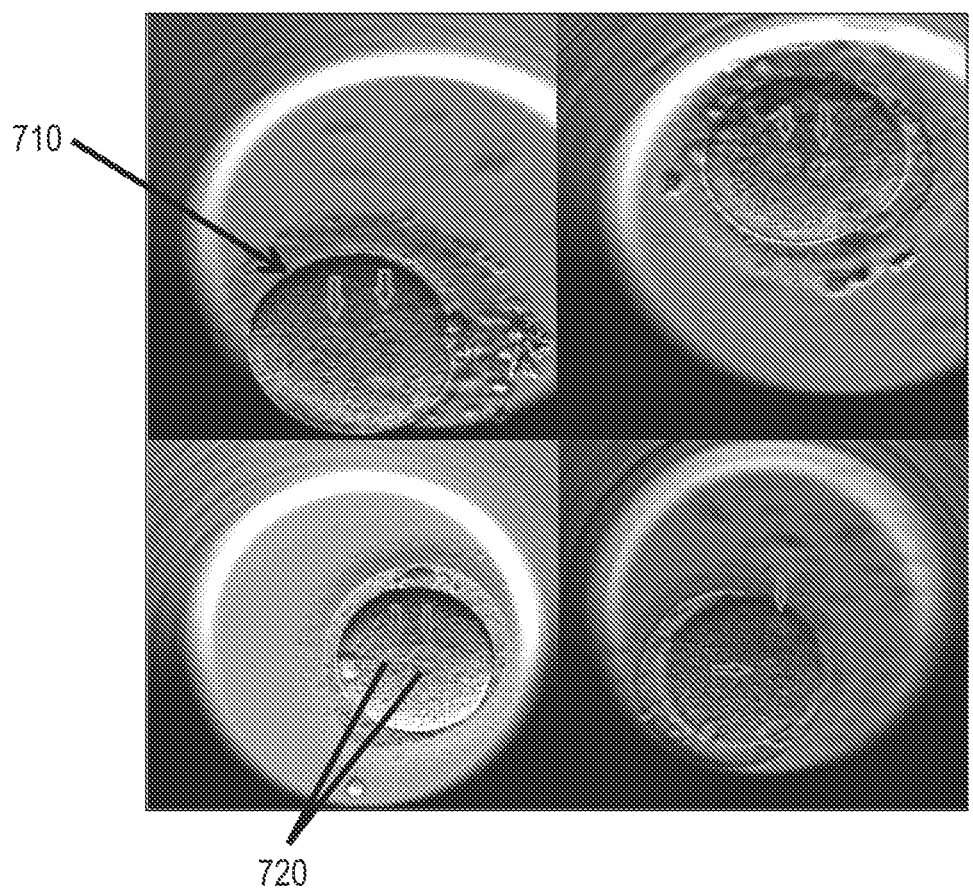
FIG. 7 depicts four images of in-vitro embryos which may be subject to the methods described herein.

FIG. 7 illustrates an example of such a feature that may need to be identified prior to IVF screening. FIG. 7 depicts four distinct images of an embryo 710 which contains two faint grey circles, called pronuclei 720. The pronucleus 720 is the nucleus of the ovum 710 which appears during the fertilisation process. They often appear at an early stage of embryo development, and they possess several unique characteristics. For example, the pronuclei 720 are often roughly circular, and they often contain nucleoli inside. The nucleoli often visually appear as small spots which may be particularly dark or particularly light compared to their surroundings. The appearance of the pronuclei 720, and their features, is often vague and varies greatly between images, due to both their actual characteristics and to artefacts of the layout and lighting. This can be seen clearly in the images of FIG. 7. The pronuclei 720 are not as easily distinguished in some of the images as others.

In order to remedy such challenges, it is possible to apply the method described herein to images of a pre-implantation embryo in order to identify the location, size and shape of the pronuclei, prior to the embryologist's examination.

As noted above, in some examples, the general concept behind the method described above may use a likelihood ratio test in which a potential feature of interest may be compared to the rest of an image (or a portion thereof) and a determination made on the basis of the pixels within the potential feature. This may provide a score, e.g. a characteristic value, which can be used to compare a potential feature with other potential features within an image. That is, there could be multiple areas which could individually qualify as a feature of interest on some levels and only in determining which of the potential features has the highest likelihood or probability of being the feature on the basis of a plurality of characteristics, is it possible to determine which is the actual feature of interest.

The use of a likelihood ratio test is a useful one as it allows a relative view to be taken of given feature. Taking a simple feature such as a black spot, this could be found by classifying all pixels as "black" and "non-black" using some criterion derived from application specific data and finding a spot full of black pixels. However, for complex features, there may be no clear separation between the values of pixels that belong to it and the values of those that do not, as determined by multiple factors including the nature of the subject being imaged and investigated. That is, what qualifies as a feature of interest may have a range of possible characteristic values in many different pixels of image data. However, every pixel has a probability of belonging to the feature or not based on the visual appearance, and the method disclosed herein may quantify this probability. This probability may then be used it to make decisions.

In the method disclosed herein, each pixel or group of pixels may receive one or more scores. Each score may be a log likelihood ratio which represents the logarithm of how common that pixel's appearance is in the feature divided by how common it is outside the feature. Thus, a pixel that is "very characteristic" of the feature receives a very high score and one which is only "weakly characteristic" of the feature receives a lower score. A pixel that is characteristic of the background rather than the feature may receive a negative score.

The more characteristics that a pixel can be classified against in this way, the better the method may accurately identify what a feature of interest may be. Hence, it will be appreciated that the selection of characteristics which are analysed may be adapted over time as new characteristics are discovered and the method can be updated incrementally.

The method may comprise determining a collective score e.g. a confidence score, for each pixel of an image. This may result in a virtual "heatmap" which may be used to provide a visualisation of a colour map indicating how relevant to a feature each pixel may be.

A sum of the scores of a set of pixels (which may be the logarithm of the product of the likelihood ratios, if each score is the logarithm of a likelihood ratio) may thus be a representation of how likely that set of pixels is to belong to the feature rather than the background.

The apparatus used to implement the invention may comprise an imager to obtain the image of the object to be assessed and one or more computing devices. The computing devices may include one or more processors and/or memories.

The image may be acquired directly from the imager or may be recalled from a storage device which may be a memory unit of the computing device or otherwise. Thus, the image may be saved as an electronic file or a series of files, which may be stored on a storage medium, such as a fixed or removable disc. The image may include metadata associated with the image and/or annotations or markings which aid the performance of the methods of the present disclosure. The computer may run software for processing the image in order to perform the method described above. The software may be stored on a carrier, such as a removable disc or a solid-state memory, or downloaded over a network such as a local area network (LAN), wide-area network (WAN), an intranet or the Internet.

Embodiments of the present disclosure may be implemented as programmable code for execution by the computer system.

The computer system may include one or more processors which may be any type of processor, including but not limited to a special purpose or a general-purpose digital signal processor. Processor may be connected to a communication infrastructure (for example, a bus or network). Computer system may also include a main memory, preferably random access memory (RAM), and may also include a secondary memory. The secondary memory may include, for example, a hard disk drive and/or a removable storage drive, representing a floppy disk drive, a magnetic tape drive, an optical disk drive, etc. A removable storage drive may read from and/or writes to a removable storage unit in a well-known manner. The removable storage unit may comprises one or more of a floppy disk, magnetic tape, optical disk, etc., which is read by and written to by removable storage drive. As will be appreciated, the removable storage unit may include a computer readable storage medium having stored therein computer software and/or data.

In alternative implementations, the secondary memory may include other similar devices for allowing computer programs or other instructions to be loaded into computer system. Such devices may include, for example, a removable storage unit and an interface. Examples of such devices may include a removable memory chip (such as an EPROM, or PROM, or flash memory) and associated socket, and other removable storage units and interfaces which allow software and data to be transferred from removable storage unit to computer system. Alternatively, the program may be executed and/or the data accessed from the removable storage unit, using the processor of the computer system.

The computer system may also include a communication interface. Communication interface may allow software and data to be transferred between computer system and external devices. Examples of communication interface may include a modem, a network interface (such as an Ethernet card), a communication port, a Personal Computer Memory Card International Association (PCMCIA) slot and card, etc. Software and data transferred via communication interface are in the form of signals, which may be electronic, electromagnetic, optical, or other signals capable of being received by communication interface.

Computer programs (also called computer control logic) may be stored in main memory and/or secondary memory. Computer programs may also be received via communication interface. Such computer programs, when executed, enable the computer system to implement the present invention as discussed herein. Accordingly, such computer programs represent controllers of computer system. Where the invention is implemented using software, the software may be stored in a computer program product and loaded into computer system using removable storage drive, hard disk drive, or communication interface, to provide some examples.

In alternative embodiments, the methods and systems of the present disclosure can be implemented as control logic in hardware, firmware, or software or any combination thereof.

As mentioned above, the present disclosure may be used in multiple different scenarios in which image analysis cannot be achieved by a human operator or state of the art computer vision or machine learning algorithms. One such area where the method may find suitable application is in identifying predictors of successful IVF implantation. Thus, embodiments of the present invention may relate to a system capable of comparing images and video of successfully implanted and non-successfully implanted embryos to thereby identify time-stamped features that are unique to successfully implanted embryos. Such features can also be correlated to EMR data (e.g. genetic markers etc.).

In Vitro Fertilization (IVF) has been used to treat infertility problems successfully since 1978. Despite on-going research, it is still a complicated procedure with a success rate of only 20% using the best available resources.

IVF is an expensive procedure that is psychologically traumatic for a patient and as such, identifying recipients for whom IVF is unlikely to be successful prior to treatment, or embryos most suitable for implantation can reduce costs associated with an IVF procedure and the discomfort such a procedure causes the patient.

One of the major problems of IVF is multiple pregnancies and associated increased foetal and maternal complications. In order to limit this problem, clinics have reduced the number of embryos transferred and, as a result, the rate of high-order multiple pregnancies has decreased dramatically in some regions. To further decrease the twin rates, elective single-embryo transfer (eSET) is widely advocated. This may result in decreased pregnancy rates compared to the transfer of two or more embryos. Increasing the pregnancy rates associated with eSET plays a major role in the decision making process of IVF labs.

Thus, the embryo selection step of an IVF procedure is crucial to implantation success.

Selection is typically carried out manually via microscopic screening of embryos throughout their development cycle. More recently, time-lapse video microscopy has enabled prolonged time lapse capture of microscopy images that can be stored for later analysis. However, the stored image data is typically analysed manually and as such, any prediction of implantation success relies on the skill and experience of the technician reviewing the captured images.

There is thus a need for, and it would be highly advantageous to have, an automated approach for qualifying embryos prior to implantation.

Unless otherwise defined, all technical and scientific terms used within the present disclosure have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present disclosure may involve performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

The present disclosure may provide a system which can be used to identify predictors of successful IVF implantation. Specifically, the present disclose may be used to process and compare images/videos of embryos successfully and unsuccessfully implanted to thereby identify predictors of successful or non-successful implantation.

Embryo selection in IVF procedures is a crucial step to implantation success. Although advancements have been made in image capture of developing embryos, analysis of captured images is still carried out by a technician and as such, the success of a procedure relies on the skill and experience of the technician. That is one of the reasons why the best IVF clinics typically have higher success rates.

While reducing the present disclosure to practice, the applicants devised an automated system for identifying predictors of successful IVF implantation from images (e.g., of time lapse videos) captured from successfully and non-successfully implanted embryos.

Thus, according to one aspect of the present disclosure there is provided a system for identifying predictors of successful IVF implantation.

As used herein, successful implantation refers to an implantation of an IVF embryo that leads to clinical pregnancy as defined by ultrasound at 6 weeks and/or live birth. Accordingly non-successful or unsuccessful implantation refer to an implantation of an IVF embryo that does not lead to implantation.

Figure 8:
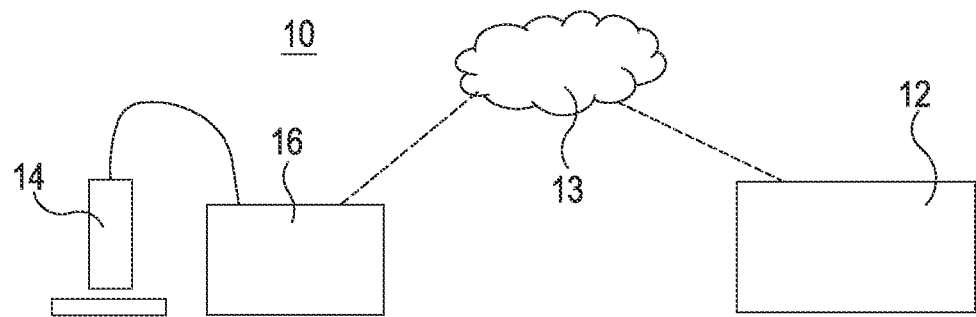
FIG. 8 is a block diagram of one example of a system according to the present disclosure.

FIG. 8 illustrates an embodiment of a system which is referred to herein as system 10. System 10 can be in communication (e.g. through cloud 13 or wire connection) with a data storage device 12 storing image sequences of qualified embryos retrieved from an image capture device 14. It will be understood that any reference to an image sequence or image sequences will include a reference to a set or plurality of such image sequences. In other words, any method steps applied to one image sequence may be applied to a set of image sequences.

System 10 includes a computing platform 16 configured for obtaining and optionally storing a first sequence of time-stamped images tracking development of a pre-implantation embryo that has been qualified as being successfully implanted and a second sequence of time-stamped images tracking development of a pre-implantation embryo that has been qualified as being non-successfully implanted.

The time-stamped images may be derived from a video capture, a time lapse capture or a still capture at various time intervals. For example, the images may be derived from stored image data that includes time lapse/video/still images obtained from 10-100 or more embryos that were subject to either eSET and subsequently successfully implanted in the uterus, or two-embryo transfer that resulted in clinical twin pregnancy and time lapse/video/still images obtained from 10-100 or more embryos that were all subject to eSET or two-embryo transfer, but resulted in no embryo implantation.

The images may be annotated as successful or unsuccessful manually or automatically (by correlating embryo with patient EMR data). The time stamp of each image will refer to the exact time when an image was recorded and reported as hours after fertilization.

In any case, the time-stamped images may represent a time period of ~150 hours in embryo development (the time from fertilization to 6 days post fertilization) from 0 hours until ~150 hours and can be spaced apart at 1 second to 20 minute intervals.

The following represents typical time points in development that can be included in the time stamped sequences of images utilized by the present invention.

t0: The time at which insemination occurs in conventional IVF. For ICSI/IMSI, where the time-lapse monitoring system and practice allows, the time of the sperm injection may be recorded, per oocyte but otherwise, it is the mid-time point from when injection begins and ends for that patient's cohort of oocytes. This time point can be used as a start time.

tPB2: The time at which the second polar body (PB2) is extruded. This is annotated at the first frame in which PB2 appears completely detached from the oolemma. The extrusion of the second polar body can be obscured depending on the position of the oocyte in the well or by cumulus cells in routine IVF insemination.

tPN: The time at which fertilization status is confirmed. It is recommended to annotate fertilization immediately before fading of pronuclei (tPNf) hence coinciding to tZ (time of pronuclear scoring), since no further observational dynamic changes are expected to occur. Appearance of individual pronuclei may be further annotated as tPNna ('n' for individual pronuclei in the order of appearance: 'a'): e.g. tPN1a, tPN2a, tPN3a the initial time at which the first, second, third, etc. pronuclei become visible.

tPNf: The time when both (or the last) PN disappear. This annotation is made at the first frame whereby the embryo is still at the 1-cell stage but pronuclei can no longer be visualized. Pronuclear fading may be further recorded according to individual pronuclei, tPN1f, tPN2f, etc. to denote the time at which the first, second or additional pronuclei fade (i.e. similar to annotation of their appearances).

tZ: The time of time-lapse PN assessment. PN are dynamic structures; they move and their morphology can change between tPNa and tPNf (Azzarello et al., 2012). It has recently been reported that the movement of the pronuclei within the cytoplasm and fading of nuclear membranes may be indicative of subsequent blastocyst development potential and hence a novel parameter providing an early indication of the embryo's developmental potential (Wirka et al., 2013). Changes in pronuclear appearance and position may coincide with movement of the nucleolar precursor bodies (NPBs) inside pronuclei, allowing differential PN scoring to be deduced. The time-lapse user group recommends annotation of PN scoring, if required, at the last frame before the pronuclei disappear (i.e. tPNf) because the alteration in pronuclear morphology has been completed.

t2: The time of the first cell cleavage, or mitosis. t2 is the first frame at which the two blastomeres are completely separated by individual cell membranes.

t3: The first observation of three discrete cells. The three cells stage marks initiation of the second round of cleavage.

tn: The first time these numbers of discrete cells are observed (until compaction of blastomeres prevents visualization of individual cells).

tSC: The first frame in which evidence of compaction is present; the initial frame that any (two) cells start to compact is observed.

tMf/p: This marks the end of the compaction process; when observable compaction is complete. The morula may be fully or partially compacted, where f is full and p is partial;

the morula has excluded material. The degree and time of compaction has been reported to be associated with blastocyst formation and quality (Ivec et al., Fertility and sterility, Volume 96, Issue 6, December 2011, Pages 1473-1478.e2 2011).

Dynamic developmental stages of blastocyst formation cannot easily be scored using existing static grading schemes (Gardner and Schoolcraft, Fertility and Sterility Volume 72, Issue 4, October 1999, Pages 604-609), for example the time when the blastocoel constitutes less than half the volume of the embryo (early blastocyst) may not be differentiated with certainty from when it is greater than or equal to half of the volume of the embryo (blastocyst). Therefore the time-lapse user group recommends employment of a novel scoring system for depicting the developmental stage of blastocysts, while it is recommended that the morphology of the inner cell mass (y) and trophectoderm (z) are graded in agreement with the static parameters within the time frame described for dynamic developmental stages, at fixed time points. This group acknowledges that blastomere biopsy may alter the dynamics of embryo development and blastocyst expansion thereby confounding morphokinetic comparisons with non-biopsied embryos (Kirkegaard et al. Human Reproduction, Volume 28, Issue 10, 1 Oct. 2013, Pages 2643-2651,). However, facilitative laser breaching of the zona pellucida, at the early cleavage stage, to facilitate herniation of trophectoderm for biopsy, has been reported not to impact downstream development to the full blastocyst stage, compared with unbreached controls (Campbell et al., 2013 *Human Reproduction*, Volume 28, Issue 10, 1 Oct. 2013, Pages 2643-2651).

tSB=initiation/start of blastulation. The first frame when initiation of a cavity formation is observed.

tByz=full blastocyst. The last frame before the zona pellucida starts to thin.

tEyz=initiation of expansion. The first frame when the zona pellucida starts to thin.

tHNyz=herniation. The first frame where extrusion of cell(s) from the zona is observed. This marks the end of the expansion phase and the initiation of the hatching process.

tHDyz=hatched blastocyst. The first frame where the embryo is detached from the zona as a whole.

Duration of Events Related to Dynamics of Early Preimplantation Period

VP is the time period in which the pronuclei are visible. It is calculated as VP (visible PN)=tPNf-tPNa. If pronuclei are annotated individually, the duration for each can be calculated (e.g. tPN1f-tPN1a).

The cell cycle is an orderly sequence of events in which a cell duplicates its contents and then divides into two. Cell cycle duration is calculated using time-lapse annotation either according to a single cell division or as a round of mitosis whereby the number of blastomeres doubles. For the first cell cycle, as development begins with the single cell, these are the same. However, the second cell cycle begins with two cells, both of which should subsequently divide, forming two daughter cells each. There are therefore two individual blastomere cell cycles but a single embryo cell cycle, which results in the doubling from two to four cells.

The embryo cell cycles (ECC) results in the doubling from two to four, and from four to eight, cells. The cell cycle for blastomere 'a' is calculated as t3-t2 and documented as cc2a, and for blastomere b as t4-t2, and documented as cc2b. The cell cycle whereby the embryo reaches four cells from two cells (ECC2) is also calculated (t4-t2). So, the time that the last cleaving blastomere takes to cleave (from t2 to t4) equates to the duration of the ECC; all individual blastomeres cleave within this time frame. The same applies for the third cell cycle. The duration of the embryo's third cycle (ECC3) is the time it takes the embryo to develop from four to eight cells, and includes four blastomere/cell cycles; a, b, c and d. cc3a is t5-t4; cc3b is t6-t4; cc3c is t7-t4 and cc3d is t8-t4. ECC3 is t8-t4.

Early embryo development follows a geometric sequence cleavage pattern {1 cell, 2 cells, 4 cells, 8 cells . . . } as mentioned above, and therefore synchronization can be measured as the time sister cells take to divide into two new cells, reaching the next step in the geometric sequence.

s2=The synchronicity of the two blastomere divisions within the second cell cycle, calculated as t4-t3.

s3=The synchronicity of the four blastomere divisions within the third cell cycle, calculated as t8-t5.

The duration of each cytokinesis may also be calculated (related to speed of the event and image capture capacity) from the first frame where a cleavage furrow is observed and the time point when cytokinesis is completed.

Duration of compaction (dcom) is the time period from initiation to cessation of compaction. For full compaction (dcom)=tMf-tSC. For partial compaction (dcom)=tMp-tSC.

Duration of blastulation (dB) is the time period from initiation of blastulation to full blastocyst formation (tB-tSB).

Duration of blastocyst expansion (dexp) is the time period from initiation of expansion to herniation (tHN-tE).

Duration of blastocyst collapse/re-expansion (dcol/dre-exp) are defined as tBCi(n) and tBCend(n), for initiation and completion of the episode, respectively, where 'n' corresponds to the subsequent episodes (for example, tBCi1=first expansion of blastocyst cavity which follows tBCend1=first collapse of the blastocoel). The duration of each phase of expansion-contraction cycle can be calculated; the initiation of collapse is annotated according to the first frame in which the blastocoel volume visibly decreased when compared with the volume (diameter) on the previous frame. The final frame prior to the initiation of re-expansion (tBCend) marks the end of the collapse episode. The period in between is the 'duration of collapse (dcol)' and is tBCend(n)-tBCi(n). The initiation of re-expansion is annotated according to the first frame in which the blastocoel volume visibly increased compared with the volume (diameter) on the previous frame. The duration of re-expansion (dre-exp) is tre-expend(n)-tre-expi(n).

Duration of herniation (dHN) is the time period from initiation of herniation to hatching (tHN-tHD).

In addition to the time-stamped image data, the present system can also gather data with respect to patient characteristics from electronic medical records (EMR). Such data can include all the medical history of the patient including blood works, radiology, medication given and medical diagnostics.

The computing platform of the present system can include software for modifying/converting the images obtained. Such modification/conversion can include colour filtering/shifting, colour inversion, image resizing, embossing, sharpening, edge enhancement and the like.

The computing platform further includes a software application for processing each image of the first and second sequences of time-stamped images in order to identify and track unique features of successfully implanted embryos. Such features can then be tagged as predictors for successful or non-successful implantation and stored by the present system for comparison with analysed images of non-qualified embryos.

As is mentioned hereinabove, the present disclosure uses approaches for qualifying embryos prior to implantation which are carried out manually by analysing a time sequence of images of a single patient. Thus, the manual approach does not compare image sequences of different embryos nor is there a need or an advantage to such a comparison.

Since the present disclosure directly compares two or more sequences of images side by side in order to identify time-stamped features unique to embryos resulting in successful or non-successful implantation, the timeline of these sequences of images must be aligned in order to ensure that the time-stamp, a crucial variable of a feature, is aligned correctly.

Thus, computing platform of the present disclosure may also include a software application for aligning the first sequence of time-stamped images with the second sequence of time stamped images such that the first sequence of time-stamped images and the second sequence of time-stamped images are development-time matched.

Such alignment can be carried out using one of several approaches. For example, the computing platform can identify a feature in each sequence of images that represents a known time point (see Tables 1-3 below). This feature can then be used to reset a timeline (e.g. time 0) for all images sequences.

The present system can analyse the images of each sequence (successful, non-successful) in order to identify differences between the images. Such differences can be image features that represent known markers of development or features that are unknown (e.g. thickness of membrane) but can be compared between two sequences of images. For various features, the system will also further analyse the images to derive an appearance time (time point when feature first appeared), disappearance time, magnitude of morphological change (in feature) over time, time length of appearance, time length of morphological change. Some features will also be correlated to a genetic marker (known from the patient EMR or from whole genome sequencing of the embryo if subjected to pre-implantation genetic testing) in order to establish a previously unknown association between feature and genetic marker (e.g., known clinical mutation/deletion/insertion).

A list of features that can be queried and annotated by the present system is provided below in Tables 1-3 along with their known time stamp.

TABLE 1

Summary of Morphokinetic variables and proposed definitions.

| Time | Definitions of expected events |
|---|---|
| t0 | Time of IVF or mid-time of micro/injection (ICSI/IMSI) |
| tPB2 | The second polar body is completely detached from the oolemma |
| tPN | Fertilization status is confirmed |
| tPNa | Appearance of individual pronuclei; tPN1a, tPN2a; tPN3a . . . |
| tPNf | Time of pronuclei disappearance; tPN1f; tPN2f . . . |
| tZ | Time of PN scoring |
| t2 to t9 | Two to nine discrete cells |
| tSC | First evidence of compaction |
| tMf/p | End of compaction process (last frame before cavity formation) 'f' corresponds to fully compacted; 'p' corresponds to partial compaction |
| tSB | Initiation of blastulation. |
| tByz | Full blastocyst (last frame before zona starts to thin) 'y' corresponds to morphology of inner cell mass; 'z' corresponds to morphology of trophectoderm cells |

TABLE 2

Summary of calculated variables of dynamic monitoring of human preimplantation embryo development.

| | Timings | | | |
|---|---|---|---|---|
| Annotations | Calculated duration of events | | Dynamic event | |
| VP | tPNf − tPNa | | PN Duration | |
| ECC1 | t2 − tPB2 | | Duration of first cell cycle | |
| ECC2 | t4 − t2 | cc2a = t3 − t2<br>cc2b = t4 − t2 | Duration of second embryo cell cycle | Duration of single blastomere cell cycle |
| ECC3 | t8 − t4 | cc3a = t5 − t4<br>cc3b = t6 − t4<br>cc3c = t7 − t4<br>cc3d = t8 − t4 | Duration of third embryo cell cycle | Duration of single blastomere cell cycle |
| s2 | t4 − t3 | | Synchronization of cell divisions | |
| s3 | t8 − t5 | | Synchronization of cleavage pattern | |
| dcom | tMf − tSC (full compaction)<br>tMp − tSC (partial compaction) | | Duration of compaction | |

TABLE 3

Summary of additional dynamics annotations

| Time | Definitions of special annotations |
|---|---|
| devent | Duration of event = t(end) − t(i) |
| tSER(i) | Appearance of SER |
| tSER(end) | Disappearance of SER |
| x%ftn | Stage-specific fragmentation<br>'x' is percentage of fragmentation<br>'tn' is last cell division that was completed |
| nMONO | 'n' is number of mononucleated blastomeres |
| nBI | 'n' is number of binucleated blastomeres |
| nMULTI | 'n' is number of multinucleated blastomeres |
| Even/Uneven cells | Symmetry of blastomere sizes |
| tTM | Trichotomous mitosis |
| tFu | Time of cell fusion |
| tPA | Time of planar blastomere arrangement |

Since the present disclosure employs algorithms for comparing images (of still or video capture) it can detect features that would otherwise go undetected by a trained technician. For example, a magnitude of morphological change (e.g., change in vesicle size or thickness of a membrane) or initial appearance of a feature that are readily recognizable by the present system can be so small or subtle that a technician would not be able to detect it or time of initial appearance of feature.

Analysis of images can be carried out by a deep learning algorithm which is an extension version of ANN (Artificial neural network).

Two main approaches for analysis can be used by the present invention in order to implement the model.

In a first approach, several different CNN (Convolutional neural network) models can be used in a pipeline process as follows:
  (i) a CNN model can be used for image segmentation and instance segmentation for each existing feature;
  (ii) an RNN model can utilize the output from the CNN model to classify the relevant state (i.e st) for each image (video frame); Each different state will have its own CNN which will be responsible for grading the quality of the state, this can also be implemented in several ways:
    (a) RNN model to predict the grade;
    (b) grade classification for each frame, and a calculated mean grade for all frames
  (iii) a DNN (deep neural network) can then process the state grades, timings and data from the medical file of the subject (EMR) to estimate the chances of the embryo transfer.

The second approach can use one or more supervised learning models:
  (i) frame by frame classification using ConvNet
  (ii) using a time-distributed ConvNet and passing the features to an RNN, in one network;
  (iii) using a 3D convolutional network;
  (iv) extracting features from each frame with a ConvNet and passing the sequence to a separate RNN;
  (v) extracting features from each frame with a ConvNet and passing the sequence to a separate MLP.

In one example, the use of the image analysis method described above in connection with any of FIGS. 1 to 7 may be implemented to determine the various morphokinetic parameters described above. Thus, for example, the image analysis method provided in FIG. 1, may be used to identify one or more characteristic features of the in vitro embryo in a first time lapse image and the same one or more characteristic features in a second lapse image. The feature may be relate to any of the parameters noted above in tables 1 to 3. For example, the features may comprise one or more of a polar body, a pronucleus, blastomeres, a blastocyst, the zona pellucida, etc. Once identified, various parameters may be measured or determined from the features such as position, size, shape, thickness of a wall or membrane, colour, texture, or orientation of the feature. Further, the dynamic behaviour of the features may be determined. Such features may include the motion, speed, growth, decay, herniation, initiation and mitosis events. In doing so, it may be possible to use the image analysis to accurately detect and measure the above referenced morphokinetic parameters as described above.

Although some of the morphokinetic parameters identified above may be known in the art, what has not been previously disclosed is how to use the morphokenitic parameters to successfully predict the viability of an in vitro embryo. In providing the system and method according to the present disclosure, the applicant has provided a reliable way of accurately identifying features such that the morphokinetic parameters can be monitored more closely.

The method of the present disclosure may include the use of only a subset of the morphokinetic parameters noted above. The method may use only two or only three of the parameters. Alternatively, the method may use any number of parameters between three and thirty different morphokinetic parameters.

In one example, the features of interest may be limited to the pronuclei. In particular, in one example, the radius, fade and movement of the pronuclei may be the only parameters used in a determination of viability.

The radius may be the average radius of the pronuclei. The average radius may be measured from the pronuclei identified using the methods of the present disclosure, in particular, those which are determined to have the highest likelihood of being pronuclei.

The average radius of each of the pronuclei may be compared with each other and a determination made as to closeness average radii. This may provide a first indicative factor of the viability of the embryo which in isolation may not be determinative, but when taken collectively with one or more of the other parameters may provide a meaningful indication.

As noted above, another parameter which may be used with the average radius is the time lapse between the fading of the pronuclei. Thus, using the method of the present disclosure, fading events of both pronuclei can be accurately assessed and more precisely monitored. As such, determining how the fades of the two pronuclei compare can be more accurately assessed also.

A further parameter may relate to the average movement which may be facilitated by the accurate recognition of the feature provided by the image analysis technique described above.

Figure 9:
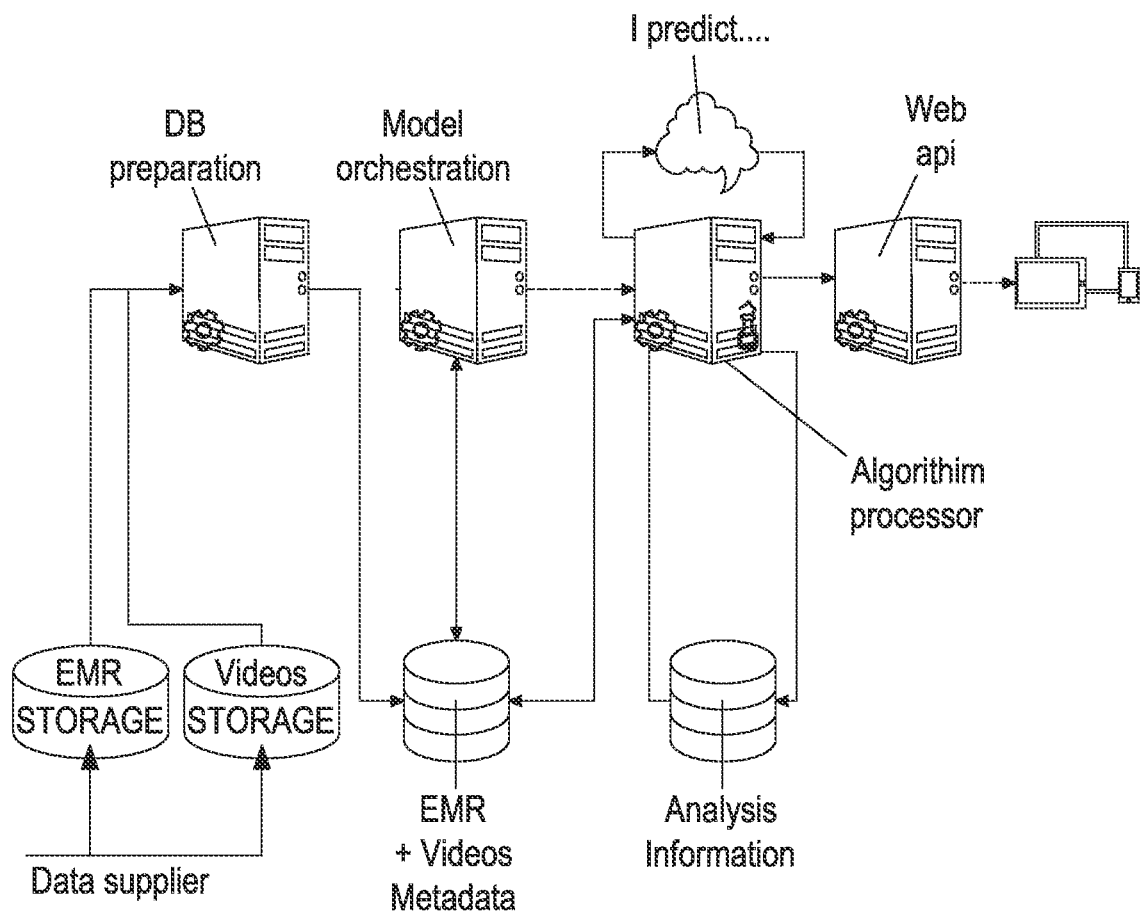
FIG. 9 is a flowchart outlining one example of a predictor-identification approach of the present disclosure.

FIG. 9 is a flow chart outlining the approach of the present invention from image sequence retrieval, through storage, preparation, addition of structured data, analysis, algorithmic paths and up to identification of features that can serve as predictors. The flow chart represents the data flow in each module in the overall architecture of the system.

In the context of the present disclosure, it may be understood that the image sequence retrieval may relate to the retrieval of the images of the sample and the feature. The image sequence may be the temporally separated images and/or the images of different focal planes. These images may then be stored (e.g. in EMR and/or video storage). These images may then be prepared for the use of any of the methods as described herein. This might involve any of the conventional image processing techniques which are known in the art. Alternatively, the preparation of the images may involve the use of the method of image processing as described herein. Structured data may then be added. The data may proceed to the analysis and algorithmic paths which may comprise the use of any of the methods described herein. Features may be identified for use as predictors, as described above. A final output from the process may be forwarded to a web API and, optionally, to an end user device such as a mobile device and/or computer.

It is expected that during the life of this patent many relevant image capturing approaches will be developed and the scope of the term image is intended to include the product of all such new technologies a priori. As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

It is to be understood that each method step as described herein may be used in combination with or separately from each other method step, and that the ordering of these method steps may be changed without departing from the scope of the invention as claimed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission.

The invention claimed is:

1. A system for identifying predictors of successful IVF implantation, wherein the system comprises:
   a memory; and
   a processor configured to:
   (a) obtain a first sequence of time-stamped images tracking development of a pre-implantation embryo that has been qualified as being successfully implanted;
   (b) obtain a second sequence of time-stamped images tracking development of a pre-implantation embryo that has been qualified as being non-successfully implanted;
   (c) computationally align said first sequence of time-stamped images with said second sequence of time stamped images such that said first sequence of time-stamped images and said second sequence of time-stamped images are development-time matched; and
   (d) computationally process each image of said first and said second sequences of time-stamped images in order to identify and track unique features of successfully implanted embryos for use as predictors of successful IVF implantation, wherein the identifying and tracking of the unique features comprises:
   determining a plurality of log likelihood ratios for each pixel or group of pixels within the image, wherein each of the plurality of the log likelihood ratios relates to a different characteristic of the unique feature; and,
   determining a confidence value for a target area of the image on the basis of the plurality of log likelihood ratios of the pixels within the target area, wherein the confidence value is indicative of whether the unique feature is represented by the target area of the image.

2. The system of claim 1, wherein (c) is effected by identifying a specific developmental feature in said first sequence of time-stamped images and said second sequence of time stamped images and setting a common development time based on said developmental feature.

3. The system of claim 1, wherein said first sequence of time-stamped images and said second sequence of time-stamped images are video sequences.

4. The system of claim 1, wherein said first sequence of time-stamped images and said second sequence of time-stamped images are time lapse sequences.

5. The system of claim 1, wherein said unique features are characterized by morphology, appearance time, disappearance time, magnitude of morphological change over time, time length of appearance, time length of morphological change and association with a genetic marker.

6. The system of claim 1, wherein the processor is further configured to modify each image of said first and said second sequences of time-stamped images prior to (d).

7. The system of claim 6, wherein said modifying is selected from the group consisting of colour shifting, colour filtering and embossing.

8. A method of identifying predictors of successful IVF implantation comprising:
   (a) obtaining a first sequence of time-stamped images tracking development of a pre-implantation embryo that has been qualified as being successfully implanted;
   (b) obtaining a second sequence of time-stamped images tracking development of a pre-implantation embryo that has been qualified as being non-successfully implanted;
   (c) computationally aligning said first sequence of time-stamped images with said second sequence of time stamped images such that said first sequence of time-stamped images and said second sequence of time-stamped images are development-time matched; and
   (d) computationally processing each image of said first and said second sequences of time-stamped images in order to identify and track unique features of successfully implanted embryos for use as predictors of successful IVF implantation, wherein the identifying and tracking of the unique features comprises:
   determining a plurality of log likelihood ratios for each pixel or group of pixels within the image, wherein each of the plurality of the log likelihood ratios relates to a different characteristic of the unique feature; and,
   determining a confidence value for a target area of the image on the basis of the plurality of log likelihood ratios of the pixels within the target area, wherein the confidence value is indicative of whether the unique feature is represented by the target area of the image.

9. The method of claim 8, wherein (c) is effected by identifying a specific developmental feature in said first sequence of time-stamped images and said second sequence of time stamped images and setting a common development time based on said developmental feature.

10. The method of claim 8, wherein said first sequence of time-stamped images and said second sequence of time-stamped images are video sequences.

11. The method of claim 8, wherein said first sequence of time-stamped images and said second sequence of time-stamped images are time lapse sequences.

12. The method of claim 8, wherein said unique features are characterized by morphology, appearance time, disappearance time, magnitude of morphological change over time, time length of appearance, time length of morphological change and association with a genetic marker.

13. The method of claim 8, wherein (d) is effected by a deep learning algorithm.

14. The method of claim 8, further comprising modifying each image of said first and said second sequences of time-stamped images prior to (d).

15. The method of claim 8, wherein said modifying is selected from the group consisting of colour shifting, colour filtering and embossing.

\* \* \* \* \*